United States Patent [19]
Miyata et al.

[11] Patent Number: 6,020,496
[45] Date of Patent: Feb. 1, 2000

[54] 5-ALKOXY-2(3H)-OXAZOLONE COMPOUNDS AND PROCESS FOR PREPARING THE SAME

[75] Inventors: Hiroyuki Miyata; Kikuo Ataka; Nobuya Satake; Masahiko Hagihara, all of Ube, Japan

[73] Assignee: Ube Industries, Ltd., Yamaguchi, Japan

[21] Appl. No.: 09/308,018

[22] PCT Filed: Nov. 14, 1997

[86] PCT No.: PCT/JP97/04157

§ 371 Date: May 12, 1999

§ 102(e) Date: May 12, 1999

[87] PCT Pub. No.: WO98/22449

PCT Pub. Date: May 28, 1998

[30] Foreign Application Priority Data

Nov. 15, 1996 [JP] Japan ................................. 8-304930

[51] Int. Cl.$^7$ .................................................. C07D 263/44
[52] U.S. Cl. ...................... 548/227; 546/271.4; 548/110; 548/205; 548/214
[58] Field of Search ...................... 548/227, 205

[56] References Cited

PUBLICATIONS

Reinecke et al *Chemical Abstracts,* vol. 128, No. 13467, Nov. 17, 99.

*Primary Examiner*—Robert W. Ramsuer
*Attorney, Agent, or Firm*—Jordan and Hamburg LLP

[57] ABSTRACT

5-Alkoxy-2(3H)-oxazolone compounds represented by general formula (1); and a process for the preparation thereof, wherein $R^1$ is hydrogen, optionally substituted $C_1$–$C_{10}$ alkyl, optionally substituted $C_3$–$C_{10}$ cycloalkyl, optionally substituted $C_2$–$C_{10}$ alkenyl or optionally substituted phenyl; $R^2$ is hydrogen, optionally substituted $C_1$–$C_{10}$ alkyl, optionally substituted phenyl or unsubstituted $C_2$–$C_{10}$ alkenyl; $R^3$ is optionally substituted $C_1$–$C_{10}$ alkyl, optionally substituted $C_3$–$C_{10}$ cycloalkyl, optionally substituted $C_2$–$C_{10}$ alkenyl excluding 2-alkenyl, or optionally substituted phenyl.

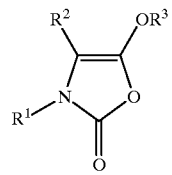

(1)

8 Claims, No Drawings

5-ALKOXY-2(3H)-OXAZOLONE COMPOUNDS AND PROCESS FOR PREPARING THE SAME

TECHNICAL FIELD

The present invention relates to a 5-alkoxy-2(3H)-oxazolone compound and a process for preparing the same.

BACKGROUND ART

The above-mentioned 5-alkoxy-2 (3H)-oxazolone compound can be led to 4-carboalkoxy-2-oxazolidinones which are useful as a synthetic starting material or an intermediate for medicines or agricultural chemicals according to the method described in the following reaction scheme (I):

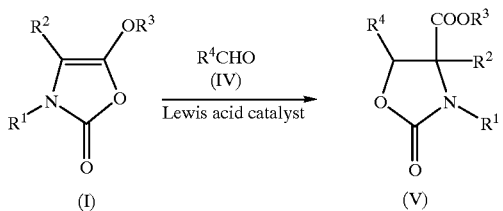

wherein $R^1$, $R^2$ and $R^3$ have the same meanings as defined below, and $R^4$ represents a $C_1$ to $C_{15}$ alkyl group, an alkenyl group, an alkynyl group or an aryl group which may be substituted.

4-Carboalkoxy-2-oxazolidinones can be easily led to β-hydroxy-α-amino acid which are useful as medical products, medical intermediate or starting materials thereof by hydrolyzing it with an alkali using an aqueous potassium hydroxide solution according to the method described in, for example, Journal of American Chemical Society, vol. 118, pp. 3584–3590 (1996).

As a conventional method for producing 4-carboalkoxy-2-oxazolidinones, the methods as mentioned below may be mentioned.

①: In Journal of Japan Chemical Society, vol. 82, p. 1075 (1961), phosgene is acted on D,L-threonine in the presence of sodium hydroxide, followed by subjecting to esterification with methanol+hydrochloric acid to obtain 5-methyl-4-carbomethoxy-2-oxazoline.

② In Journal of Japan Chemical Society, vol. 82, p. 1075 (1961), there is described a method in which N-Cbz-D,L-allothoreonine is subjected to ring opening in the presence of sodium hydroxide, followed by esterification of the resulting compound with methanol+hydrochloric acid to obtain 5-methyl-4-carbomethoxy-2-oxazolidinone.

③: In Journal of Organic Chemistry, vol. 44, p. 3967, (1979), there is disclosed that N-carbobenzyloxyglycine ethyl ester is reacted with benzaldehyde in the presence of lithium diisopropylamide to obtain 5-phenyl-4-carbomethoxy-2-oxazolidinone.

④: In Tetrahedron Letters, vol. 29, p. 2069, (1988), there is disclosed a method of obtaining 3-methyl-5-(1-methyl-3-pentenyl)-4-carbomethoxy-2-oxazolidinone by reacting 3-(1-methyl-3-pentenyl)-2,3-epoxy-1-propanol and methyl isocyanate to obtain 4-hydroxymethyloxazolidine and oxidizing it with a chromium compound, and further esterifying the resulting compound with diazomethane.

However, a preparing process which passes through 5-alkoxy-2 (3H)-oxazolone compound has not yet been known as of today.

An object of the present invention is to provide a novel 5-alkoxy-2(3H)-oxazolone compound which is useful as a synthetic starting material or an intermediate of medicines or agricultural chemicals and a process for preparing the same.

DISCLOSURE OF THE INVENTION

The present inventors have investigated to solve the above problems, and as a result, they have found that a novel 5-alkoxy-2(3H)-oxazolone compound which can be obtained easily with a high yield can be used as a synthetic starting material for 4-carboalkoxy-2-oxazolidinones, whereby accomplished the present invention.

That is, the present invention relates to a 5-alkoxy-2(3H)-oxazolone compound represented by the formula (I):

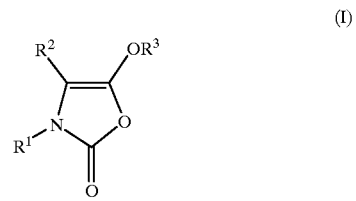

wherein R represents a hydrogen atom, a $C_1$ to $C_{10}$ alkyl group which may be substituted, a $C_3$ to $C_{10}$ cycloalkyl group which may be substituted, a $C_2$ to $C_{10}$ alkenyl group which may be substituted or a phenyl group which may be substituted; $R^2$ represents a hydrogen atom, a $C_1$ to $C_{10}$ alkyl group which may be substituted, a phenyl group which may be substituted or an unsubstituted $C_2$ to $C_{10}$ alkenyl group; and $R^3$ represents a $C_1$ to $C_{10}$ alkyl group which may be substituted, a $C_3$ to $C_{10}$ cycloalkyl group which may be substituted, a $C_2$ to $C_{10}$ alkenyl group which may be substituted (provided that a 2-alkenyl group is excluded) or a phenyl group which may be substituted.

Moreover, the present invention relates to a process for preparing the 5-alkoxy-2 (3H)-oxazolone compound represented by the above formula (I) which comprises reacting an N-substituted-α-amino acid ester represented by the formula (II):

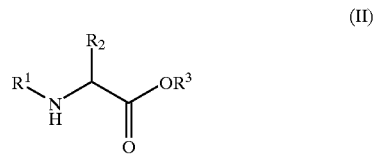

wherein $R^1$, $R^2$ and $R^3$ have the same meanings as defined above, and a chloroformylating agent in the presence of a base (1) in a solvent to convert it to a compound represented by the formula (III):

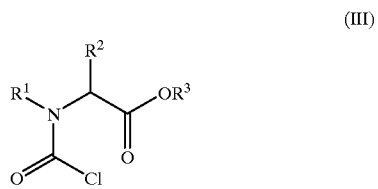

wherein $R^1$, $R^2$ and $R^3$ have the same meanings as defined above, and then, subjecting to intramolecular cyclization reaction in the presence of a base (2).

BEST MODE FOR PRACTICING THE INVENTION

In the present invention, $R^1$ in the 5-alkoxy-2(3H)-oxazolone compound (hereinafter also referred to as "Compound (I)") represented by the formula (I) represents a hydrogen atom, a $C_1$ to $C_{10}$ alkyl group which may be substituted, a $C_2$ to $C_{10}$ alkenyl group which may be substituted, a $C_3$ to $C_{10}$ cycloalkyl group which may be substituted or a phenyl group which may be substituted. The "$C_1$ to $C_{10}$ alkyl group which may be substituted" represented by R1 means (1) "a $C_1$ to $C_{10}$ alkyl group having no substituent" or (2) "a $C_1$ to $C_{10}$ alkyl group having a substituent(s)".

As "the $C_1$ to $C_{10}$ alkyl group having no substituent" of (1), there may be mentioned, for example, a $C_1$ to $C_{10}$ straight or branched alkyl group such as a methyl group, an ethyl group, a propyl group (including an isomer thereof), a butyl group (including respective isomers thereof), a pentyl group (including respective isomers thereof), a hexyl group (including respective isomers thereof), a heptyl group (including respective isomers thereof), an octyl group (including respective isomers thereof), a nonyl group (including respective isomers thereof) or a decyl group (including respective isomers thereof), preferably a $C_1$ to $C_4$ alkyl group, more preferably a methyl group, an ethyl group, a propyl group, an isopropyl group, a butyl group, an isobutyl group, a sec-butyl group or a tert-butyl group.

A $C_1$ to $C_{10}$ alkyl group in "the $C_1$ to $C_{10}$ alkyl group having a substituent(s)" of (2) has the same meaning as in "the $C_1$ to $C_{10}$ alkyl group having no substituent" of (1).

As the substituent of "the $C_1$ to $C_{10}$ alkyl group having a substituent(s)" of (2), there may be mentioned, for example, a cyano group, a benzyloxy group a phthalimido group, an alkoxycarbonyl group, a trialkylsilyloxy group, an acylamino group, a halogen atom such as a fluorine atom, a chlorine atom, a bromine atom and an iodine atom, an aryl group which may be substituted, "a 5- or 6-membered heteroaromatic ring group containing one or two hetero atom(s) selected from N, O and S (hereinafter also referred to as a heteroaromatic ring group)" which may be substituted or a $C_1$ to $C_{10}$ alkoxy group which may be substituted.

As the acylamino group which is a substituent of "the alkyl group having a substituent(s)" of (2), there may be mentioned, for example, a formamido group, an acetamido group, a chloroacetamido group, a benzoylamido group, a phenylacetamido group, a methoxycarbonylamino group, an ethoxycarbonylamino group, an allyloxycarbonylamino group, a tert-butoxycarbonylamino group or a benzyloxycarbonylamino group, preferably a formamido group, an acetamido group, a benzoylamido group, a methoxycarbonylamino group, a tert-butoxycarbonylamino group or a benzyloxycarbonylamino group, more preferably an acetamido group, a tert-butoxycarbonylamino group or a benzyloxycarbonylamino group.

As the alkoxycarbonyl group which is a substituent of "the alkyl group having a substituent(s)" of (2), there may be mentioned, for example, an alkoxycarbonyl group having a straight or branched $C_1$ to $C_6$ alkyl group portion such as a methoxycarbonyl group, an ethoxycarbonyl group, a n-propoxycarbonyl group, an isopropoxycarbonyl group, a n-butoxycarbonyl group, a sec-butoxycarbonyl group, a tert-butoxycarbonyl group, a n-pentenyloxycarbonyl group or a n-hexyloxycarbonyl group.

As the trialkylsilyloxy group which is a substituent of "the alkyl group having a substituent(s)" of (2), there may be mentioned, for example, a trialkylsilyloxy group having the same or different straight or branched $C_1$ to $C_6$ alkyl group portion(s) such as a trimethylsilyloxy group, a triethylsilyloxy group, a triisopropylsilyloxy group, a dimethylisopropylsilyloxy group, a tert-butyldimethylsilyloxy group, a tripentylsilyloxy group or a trihexylsilyloxy group.

"The aryl group which may be substituted" which is a substituent of "the $C_1$ to $C_{10}$ alkyl group having a substituent (s)" of (2) means (2-1) "an aryl group having no substituent" or (2-2) "an aryl group having a substituent(s)

As "the aryl group having no substituent" of (2-1), there may be mentioned, for example a phenyl group, a naphthyl group, an anthryl group or a phenanthryl group, etc., preferably a phenyl group, a naphthyl group or an anthryl group, more preferably a phenyl group or a naphthyl group.

The aryl group of "the aryl group having a substituent(s)" of (2-2) has the same meaning as "the aryl group having no substituent" of (2-1). As the substituent of "the aryl group having a substituent(s)" of (2-2), there may be mentioned, for example, a nitro group; a cyano group; a benzyloxy group; the alkoxycarbonyl group as mentioned above; the trialkylsilyloxy group as mentioned above; the halogen atom as mentioned above; a straight or branched $C_1$ to $C_6$ alkyl group such as a methyl group, an ethyl group, a propyl group (including an isomer thereof), a butyl group (including respective isomers thereof), a pentyl group (including respective isomers thereof) or a hexyl group (including respective isomers thereof); or a straight or branched $C_1$ to $C_6$ alkoxy group such as a methoxy group, an ethoxy group, a propoxy group (including an isomer thereof), a butoxy group (including respective isomers thereof), a pentyloxy group (including respective isomers thereof) or a hexyloxy group (including respective isomers thereof), preferably a $C_1$ to $C_6$ alkyl group, a $C_1$ to $C_6$ alkoxy group, a halogen atom, a benzyloxy group or a nitro group, more preferably a straight or branched $C_1$ to $C_6$ alkyl group such as a methyl group, an ethyl group, a propyl group (including an isomer thereof), a butyl group (including respective isomers thereof), a pentyl group (including respective isomers thereof) or a hexyl group (including respective isomers thereof).

"The heteroaromatic ring group which may be substituted" which is a substituent of "the $C_1$ to $C_{10}$ alkyl group having a substituent(s)" of (2) means (2-3) "a heteroaromatic ring group having no substituent" or (2-4) "a heteroaromatic ring group having a substituent(s)".

As the heteroaromatic ring group of "the heteroaromatic ring group having no substituent" of (2-3), there may be mentioned, for example, a furyl group, a thienyl group, a pyrrolyl group, a 2H-pyrrolyl group, an oxazolyl group, an isoxazolyl group, a thiazolyl group, an isothiazolyl group, an imidazolyl group, a pyrazolyl group, a pyranyl group, a pyridyl group, a pyridazinyl group, a pyrimidinyl group or a pyrazinyl group, etc., preferably a furyl group, a thienyl group, a pyridyl group, an oxazolyl group, more preferably a furyl group.

The heteroaromatic ring group of "the heteroaromatic ring group having a substituent(s)" of (2-4) has the same meaning as "the heteroaromatic ring group having no substituent" of (2-3).

As the substituent(s) of "the heteroaromatic ring group having a substituent(s)" of (2-4), there may be mentioned, for example, a nitro group, a cyano group, a benzyloxy group, the alkoxycarbonyl group as mentioned above, the trialkylsilyl group as mentioned above, the halogen atom as mentioned above, the $C_1$ to $C_6$ alkyl group "described as the substituent of "the aryl group having a substituent(s)" of (2-2)" or the $C_1$ to $C_6$ alkoxy group "described as the substituent of "the aryl group having a substituent(s)" of (2-2)", preferably a $C_1$ to $C_6$ alkyl group, a $C_1$ to $C_6$ alkoxy group, a benzyloxy group, a halogen atom or a nitro group, more preferably a methyl group, an ethyl group, a propyl group (including an isomer thereof), a butyl group (including respective isomers thereof), a pentyl group (including respective isomers thereof) or a hexyl group (including respective isomers thereof). Incidentally, the number of the substituent(s) and the position thereof are not limited.

"The $C_1$ to $C_{10}$ alkoxy group which may be substituted" which is a substituent of "the $C_1$ to $C_{10}$ alkyl group having a substituent(s)" of (2) means (2-5) "a $C_1$ to $C_{10}$ alkoxy group having no substituent" or (2-6) "a $C_1$ to $C_{10}$ alkoxy group having a substituent(s)".

As "the $C_1$ to $C_{10}$ alkoxy group having no substituent" of (2-5), there may be mentioned, for example, a straight or branched $C_1$ to $C_{10}$ alkoxy group such as a methoxy group, an ethoxy group, a propoxy group (including an isomer thereof), a butoxy group (including respective isomers thereof), a pentyloxy group (including respective isomers thereof), a hexyloxy group (including respective isomers thereof), a heptyloxy group (including respective isomers thereof), an octyloxy group (including respective isomers thereof), a nonyloxy group (including respective isomers thereof) or a decyloxy group (including respective isomers thereof), preferably a methoxy group, an ethoxy group, a propoxy group or a tert-butoxy group, more preferably a methoxy group.

The $C_3$ to $C_{10}$ alkoxy group of "the $C_1$ to $C_{10}$ alkoxy group having a substituent(s)" of (2-6) has the same meaning as "the $C_1$ to $C_{10}$ alkoxy group having no substituent" of (2-5). As the substituent(s) of "the $C_1$ to $C_{10}$ alkoxy group having a substituent(s)" of (2-6), there maybe mentioned, for example, a benzyloxy group, a phenoxy group, a methoxyethoxy group, the trialkylsilyloxy group as mentioned above, or the $C_1$ to $C_6$ alkoxy group "described as the substituent of "the aryl group having a substituent(s)" of (2-2)", preferably a methoxy group, an ethoxy group, a benzyloxy group or a methoxyethoxy group, more preferably a methoxy group or a benzyloxy group. Incidentally, the number of the substituent(s) and the position thereof are not limited.

"The cycloalkyl group which may be substituted" represented by $R^1$ in the compound (I) means (3) "a $C_3$ to $C_{10}$ cycloalkyl group having no substituent" or (4) "a $C_3$ to $C_{10}$ cycloalkyl group having a substituent(s)".

As "the $C_3$ to $C_{10}$ cycloalkyl group having no substituent" of (3), there may be mentioned, for example, a cyclopropyl group, a cyclobutyl group, a cyclopentyl group, a cyclohexyl group, a cycloheptyl group, a cyclooctyl group, a cyclononyl group or a cyclodecyl group, preferably a $C_3$ to $C_{10}$ cycloalkyl group, more preferably a cyclohexyl group.

The $C_3$ to $C_{10}$ cycloalkyl group of "the $C_3$ to $C_{10}$ cycloalkyl group having a substituent(s)" of (4) has the same meaning as "the $C_3$ to $C_{10}$ cycloalkyl group having no substituent" of (3). As the substituent(s) of "the $C_3$ to $C_{10}$ cycloalkyl group having a substituent(s)" of (4), there may be mentioned, for example, a cyano group, a benzyloxy group, the alkoxycarbonyl group as mentioned above, the trialkylsilyloxy group as mentioned above, the acylamino group as mentioned above, the halogen atom as mentioned above, the $C_1$ to $C_6$ alkyl group "described as the substituent of "the aryl group having a substituent(s)" of (2-2)", the aryl group "described at (2-1) and (2-2)" or the $C_1$ to $C_6$ alkoxy group "described as the substituent of "the aryl group having a substituent(s)" of (2-2)", preferably a benzyloxy group, a $C_1$ to $C_6$ alkyl group, an aryl group or a $C_1$ to $C_6$ alkoxy group, more preferably a phenyl group, a naphthyl group, an anthryl group, a phenanthryl group, a methyl group, an ethyl group, a propyl group (including an isomer thereof), a butyl group (including respective isomers thereof), a pentyl group (including respective isomers thereof), a hexyl group (including respective isomers thereof), a methoxy group, an ethoxy group, a propoxy group (including an isomer thereof), a butoxy group (including respective isomers thereof), a pentyloxy group (including respective isomers thereof), a hexyloxy group (including respective isomers thereof). Incidentally, the number of the substituent(s) and the position thereof are not limited.

"The $C_2$ to $C_{10}$ alkenyl group which may be substituted" represented by $R^1$ in the compound (I) has the same meaning as (5) "a $C_2$ to $C_{10}$ alkenyl group having no substituent" or (6) "a $C_2$ to $C_{10}$ alkenyl group having a substituent(s)".

As "the $C_2$ to $C_{10}$ alkenyl group having no substituent" of (5), there may be mentioned, for example, a straight or branched $C_2$ to $C_{10}$ alkenyl group such as an ethynyl group, a propenyl group (including an isomer thereof), a butenyl group (including respective isomers thereof), a pentenyl group (including respective isomers thereof), a hexenyl group (including respective isomers thereof), a heptenyl group (including respective isomers thereof), an octaneyl group (including respective isomers thereof), a nonenyl group (including respective isomers thereof) or a decenyl group (including respective isomers thereof), preferably a $C_2$ to $C_4$ alkenyl group, more preferably an ethynyl group or a propenyl group.

The $C_2$ to $C_{10}$ alkenyl group of "the $C_2$ to $C_{10}$ alkenyl group having a substituent(s)" of (6) has the same meaning as "the $C_2$ to $C_{10}$ alkenyl group having no substituent" of (5). As the substituent(s) of "the $C_2$ to $C_{10}$ alkenyl group having a substituent(s)" of (6), there may be mentioned, for example, a cyano group, a benzyloxy group, the alkoxycarbonyl group as mentioned above, the trialkylsilyloxy group as mentioned above, the halogen atom as mentioned above, the aryl group "described at (2-1) and (2-2)", the heteroaromatic ring group "described at (2-3) and (2-4)" or the $C_1$ to $C_6$ alkoxy group "described as the substituent of "the aryl group having a substituent(s)" of (2-2)", preferably a halogen atom, an aryl group "described at (2-2)", a heteroaromatic ring group "described at (2-4)" or a $C_1$ to $C_6$ alkoxy group, more preferably a phenyl group, a naphthyl group, an anthryl group or a phenanthryl group. Incidentally, the number of the substituent(s) and the position thereof are not limited.

"The phenyl group which may be substituted" represented by $R^1$ in the compound (I) means a phenyl group or "a phenyl group having a substituent(s)". As the substituent(s) of "the phenyl group having a substituent(s)", there may be mentioned, for example, a straight or branched $C_1$ to $C_6$ alkyl group such as a methyl group, an ethyl group, a propyl group (including an isomer thereof), a butyl group (including respective isomers thereof), a pentyl group (including respective isomers thereof) or a hexyl group (including respective isomers thereof); a nitro group, a benzyloxy group, the halogen atom as mentioned above; an acylamino group such as a formamido group, an acetamido group, a benzoylamido group, a methoxycarbonylamino group; or a straight or branched $C_1$ to $C_6$ alkoxy group such as a methoxy group, an ethoxy group, a propoxy group (including an isomer thereof), a butoxy group (including respective isomers thereof), a pentyloxy group (including respective isomers thereof), a hexyloxy group (including respective isomers thereof), preferably a methyl group, an ethyl group, a propyl group (including an isomer thereof), a butyl group (including respective isomers thereof), a nitro group, a halogen atom, a benzyloxy group or a $C_1$ to $C_6$ alkoxy group, more preferably a methyl group, a fluorine atom, a chlorine atom, a bromine atom, an iodine atom, a benzyloxy group or a methoxy group.

Specific examples of such $R^1$ may include, for example, a hydrogen atom, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-cyanoethyl group, a 1-carbomethoxyethyl group, a 2-trimethylsilyloxyethyl group, a 2-benzyloxyethyl group, a 2-trifluoroethyl group, a 2-chloroethyl group, a benzyl group, a 4-nitrobenzyl group, a cyanobenzyl group, a 4-carbomethoxybenzyl group, a 4-trimethylsilyloxybenzyl group, a 4-benzyloxybenzyl group, a 3,4-difluorobenzyl group, a 4-methylbenzyl group, an 2-methylbenzyl group, a 3,4-dichlorobenzyl group, an 2-fluorobenzyl group, a 4-fluorobenzyl group, a 2,4-dimethylbenzyl group, a 4-isopropylbenzyl group, a 4-tert-butylbenzyl group, an 4-methoxybenzyl group, a 3-methoxybenzyl group, a 3-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a (1-naphthyl)methyl group, a 1-phenylethyl group, a 1-(p-nitrophenyl)ethyl group, a 1-(4-bromophenyl)ethyl group, a 1-(4-fluorophenyl)ethyl group, a 1-(4-methoxyphenyl)ethyl group, a 1-(4-chlorophenyl)ethyl group, a 1-(1-naphthyl) ethyl group, a 1-(2-naphthyl)ethyl group, a diphenylmethyl group, a di(4-chlorophenyl)methyl group, a di(4-methoxyphenyl)methyl group, a trityl group, a 1- (2-phenanthryl) ethyl group, a 1- (9-anthranyl) ethyl group, a furfuryl group, a 2-thienylmethyl group, a 2-pyridylmethyl group, a 3-pyridylmethyl group, an isothiazolylmethyl group, a 2-pyrazolylethyl group, a (2H-pyrrolyl) group, a (N-methylpyrrolyl)methyl group, an isoxazolylmethyl group, a 2-methoxyethyl group, a 2-ethoxyethyl group, a 2-(n-propoxy)ethyl group, a 2-isopropoxyethyl group, a 3-(n-butoxy)propyl group, a 2-(sec-butoxy)ethyl group, a 2-(tert-butoxy)ethyl group, a 2-hexyloxyethyl group, a 2-methoxy-n-butyl group, a 2- (tert-butoxy)-1, 1-dimethyl-ethyl group, a 2-octyloxyethyl group, a 2-nonyloxyethyl group, a 2-heptyloxyethyl group, a 2-methoxyethoxyethyl group, a 2-(benzyloxymethoxy)-ethyl group, a 2-(2-methoxyethoxy-methoxy)ethyl group, a 2-(ethoxymethoxy)-ethyl group, a 2-(phenoxymethoxy)-ethyl group, a 2-formamidoethyl group, a 2-acetamidoethyl group, a 2-chloroacetamidoethyl group, a 2-benzoylamidoethyl group, a 2-phenylacetamidoethyl group, a 2-methoxycarbonylaminoethyl group, a 2-ethoxycarbonylaminoethyl group, a 2-allyloxycarbonylaminoethyl group, a 2-tert-butoxycarbonylaminoethyl group, a 2-benzyloxycarbonylaminoethyl group, an ethenyl group, a propenyl group, a butenyl group, a pentenyl group, a hexenyl group, a heptenyl group, an octenyl group, a nonenyl group, a decenyl group, a 2-cyanoethynyl group, a 1-carbomethoxy-2-propenyl group, a 1-trimethylsilylmethyl-2-propenyl group, a 1-benzyloxymethyl-2-propenyl group, a cinnamyl group, a 2-methoxymethyl-2-propenyl group, a 2-ethoxymethyl-2-propenyl group, a cyclopropyl group, a cyclobutyl group, a cyclopentyl group, a cyclohexyl group, a cycloheptyl group, a cyclooctyl group, a cyclononyl group, a cyclodecyl group, a 1-carbomethoxycyclopropyl group, a 2-phenylcyclopropyl group, a 2-fluorocyclopropyl group, a 2-chlorocyclopropyl group, a 2-benzyloxymethylpentyl group, a 1-cyanopentyl group, a 2-norbornyl group, a bornyl group, a 1-adamantyl group, a 4-methylcyclohexyl group, a 2-methylcyclohexyl group, a 2,3-dimethylcyclohexyl group, a 1-carbomethoxycyclohexyl group, a 2-methoxycyclohexyl group, a 2-trimethylcyclohexyl group, a 2-benxyloxycyclohexyl group, a 4-benzyloxycyclohexyl group, a 4-tert-butylcyclohexyl group, a menthyl group, a 8-phenylmentyl group, a phenyl group, a 2-methylphenyl group, a 3-methylphenyl group, a 4-methylphenyl group, a 4-tert-butylphenyl group, a 3,4-dimethylphenyl group, a 4-ethylphenyl group, a 2-chlorophenyl group, a 3-chlorophenyl group, a 4-chlorophenyl group, a 2-fluorophenyl group, a 3-fluorophenyl group, a 4-fluorophenyl group, a 2-bromophenyl group, a 3-bromophenyl group, a 4-bromophenyl group, a 2-iodophenyl group, a 4-iodophenyl group, a 4-methoxyphenyl group, a 3,4-dimethoxyphenyl group, a 2-benzyloxyphenyl group, a 4-benzyloxyphenyl group, a 3,4-dibenzyloxyphenyl group, a 2-methoxyphenyl group, a 3-methoxyphenyl group or a 4-nitrophenyl group, preferably a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-cyanoethyl group, a 1-carbomethoxyethyl group, a 2-trimethylsilyloxyethyl group, a 2-benzyloxyethyl group, a 2-trifluoroethyl group, a 2-chloroethyl group, a benzyl group, a 4-nitrobenzyl group, a cyanobenzyl group, a 4-carbomethoxybenzyl group, a 4-trimethylsilyloxybenzyl group, a 4-benzyloxybenzyl group, a 3,4-dichlorobenzyl group, a 2-fluorobenzyl group, a 4-fluorobenzyl group, a 3,4-difluorobenzyl group, a 4-methylbenzyl group, a 2-methylbenzyl group, a 2,4-dimethylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a (1-naphthyl)methyl group, a 1-phenylethyl group, a 1-(4-nitrophenyl)ethyl group, a 1-(4-bromophenyl)ethyl group, a 1-(4-fluorophenyl)ethyl group, a 1-(4-methoxyphenyl)ethyl group, a 1-(4-chlorophenyl)ethyl group, a 1-(1-naphthyl)-ethyl group, a 1-(2-naphthyl)ethyl group, a diphenylmethyl group, a di(4-chlorophenyl)methyl group, a di(4-methoxyphenyl) methyl group, a trityl group, a 1- (2-phenanthryl) ethyl group, a 1-(9-anthranyl)ethyl group, a furfuryl group, a 2-thienylmethyl group, a 2-pyridylmethyl group, a 3-pyridylmethyl group, a 2-methoxyethyl group, a 2-ethoxyethyl group, a 2-(n-propoxy)ethyl group, a 2-isopropoxyethyl group, a 3-(n-butoxy)propyl group, a 2-(sec-butoxy)ethyl group, a 2-(tert-butoxy)ethyl group, a 2-hexyloxyethyl group, a 2-methoxy-n-butyl group, a 2-(tert-butoxy)-1, 1-dimethyl-ethyl group, a 2-octyloxyethyl group, a 2-nonyloxyethyl group, a 2-methoxyethoxyethyl group, a 2-(benzyloxymethoxy)-ethyl group, a 2-(2-methoxyethoxymethoxy)ethyl group, a 2-(ethoxymethoxy)-ethyl group, a 2-(phenoxymethoxy)-ethyl group, a 2-formamidoethyl group, a 2-acetamidoethyl group, a 2-chloroacetamidoethyl group, a 2-benzoylamidoethyl group, a 2-phenylacetamidoethyl group, a 2-methoxycarbonylaminoethyl group, a 2-ethoxycarbonylaminoethyl group, a 2-allyloxycarbonylaminoethyl group, a 2-tert-butoxycarbonylaminoethyl group, a 2-benzyloxycarbonylaminoethyl group, a phenyl group, a 4-methylphenyl group, a 4-tert-butylphenyl group, a 3,4-dimethylphenyl group, a 4-ethylphenyl group, a 2-chlorophenyl group, a 3-chlorophenyl group, a 4-chlorophenyl group, a 2-fluorophenyl group, a 3-fluorophenyl group, a 4-fluorophenyl group, a 2-bromophenyl group, a 3-bromophenyl group, a 4-bromophenyl group, a 2-iodophenyl group, a 4-iodophenyl group, a 4-methoxyphenyl group, a 3,4-dimethoxyphenyl group, a 2-benzyloxyphenyl group, a 4-benzyloxyphenyl group, a 3,4-dibenzyloxyphenyl group, a 2-methoxyphenyl group, a 3-methoxyphenyl group or a 4-nitrophenyl group, more preferably a benzyl group, a 4-methylbenzyl group, a 1 phenylethyl group, a diphenylmethyl group, a (1-naphthyl)methyl group, a 1-(1-naphthyl) ethyl group, a 3,4-dimethoxybenzyl group, a furfuryl group, an isopropyl group or a phenyl group.

In the present invention, $R^2$ in the compound (I) represents a hydrogen atom, a $C_1$ to $C_{10}$ alkyl group which may be substituted, a phenyl group which may be substituted or an unsubstituted $C_2$ to $C_{10}$ alkenyl group.

"The $C_1$ to $C_{10}$ alkyl group which may be substituted" shown by R2 means (7) "a $C_1$ to $C_{10}$ alkyl group having no substituent" or (8) "a $C_1$ to $C_{10}$ alkyl group having a substituent(s)".

As "the $C_1$ to $C_{10}$ alkyl group having no substituent" of (7), there may be mentioned, for example, a straight or branched $C_1$ to $C_{10}$ alkyl group such as a methyl group, an ethyl group, a propyl group (including an isomer thereof), a butyl group (including respective isomers thereof), a pentyl group (including respective isomers thereof), a hexyl group (including respective isomers thereof), a heptyl group (including respective isomers thereof), an octyl group (including respective isomers thereof), a nonyl group (including respective isomers thereof) or a decyl group (including respective isomers thereof) , preferably a $C_1$ to $C_6$ alkyl group, more preferably a methyl group, an ethyl group, a propyl group or a butyl group.

A $C_1$ to $C_{10}$ alkyl group in "the $C_1$ to $C_{10}$ alkyl group having a substituent(s)" of (8) has the same meaning as in "the $C_1$ to $C_{10}$ alkyl group having no substituent" of (7). As the substituent of "the $C_1$ to $C_{10}$ alkyl group having a substituent(s)" of (8), there may be mentioned, for example, a phthalimido group, a benzyloxy group, the alkoxycarbonyl group as mentioned above, the trialkylsilyloxy group as mentioned above, a $C_1$ to $C_{10}$ alkoxy group "mentioned at (2-5)", a $C_1$ to $C_{10}$ alkylthio group mentioned below, the acylamino group as mentioned above, the halogen atom as mentioned above, the aryl group "mentioned at (2-1) and (2-2)" or the heteroaromatic ring group "mentioned at (2-3) and (2-4)".

"The aryl group which may be substituted" as a substituent(s) of "the $C_1$ to $C_{10}$ alkyl group having a substituent(s)" of (8) means (8-1) "an aryl group having no substituent" or (8-2) "an aryl group having a substituent(s)".

As "the aryl group having no substituent" of (8-1), there may be mentioned, for example, a phenyl group or a naphthyl group. The aryl group of "the aryl group having a substituent(s)" of (8-2) has the same meaning as "the aryl group having no substituent" of (8-1).

As the substituent(s) of "the aryl group having a substituent(s) of (8-2), there may be mentioned, for example, a straight or branched $C_1$ to $C_6$ alkyl group such as a methyl group, an ethyl group, a propyl group (including an isomer thereof), a butyl group (including respective isomers thereof), a pentyl group (including respective isomers thereof) or a hexyl group (including respective isomers thereof), a nitro group, a benzyloxy group, the halogen group as mentioned above, a formamido group, an acetamido group, a benzoylamido group, an acylamino group such as a methoxycarbonylamino group, a tert-butoxycarbonylamino group or a benzyloxycarbonylamino group, a straight or branched $C_1$ to $C_6$ alkoxy group such as a methoxy group, an ethoxy group, a propyl group (including an isomer thereof), a butoxy group (including respective isomers thereof), a pentyloxy group (including respective isomers thereof) or a hexyloxy group (including respective isomers thereof), preferably a halogen atom, a benzyloxy group or a $C_1$ to $C_6$ alkoxy group, more preferably a fluorine atom, a chlorine atom, a bromine atom, an iodine atom or a benzyloxy group.

"The heteroaromatic ring group which may be substituted" which is a substituent(s) of "the $C_1$ to $C_{10}$ alkyl group having a substituent(s)" of (8) means (8-3) "a heteroaromatic ring group having no substituent" or (8-4) "a heteroaromatic ring group having a substituent(s)".

As the heteroaromatic ring group of "the heteroaromatic ring group having no substituent" of (8-3), there may be mentioned, for example, a furyl group, a thienyl group, an oxazolyl group, an isoxazolyl group, a thiazolyl group, an indolyl group or an imidazolyl group, preferably a furyl group or a thienyl group. The heteroaromatic ring group of "the heteroaromatic ring group having a substituent(s)" of (8-4) has the same meaning as "the heteroaromatic ring group having no substituent" of (8-3). As the substituent(s) of "the heteroaromatic ring group having a substituent(s)" of (8-4), there may be mentioned, for example, the $C_1$ to $C_6$ alkyl group "described as the substituent of "the aryl group having a substituent(s)" of (8-2)" or the halogen atom as mentioned above.

As "the $C_1$ to $C_{10}$ alkoxy group" which is a substituent(s) of "the $C_1$ to $C_{10}$ alkyl group having a substituent(s)" of (8), there may be mentioned, for example, a straight or branched $C_1$ to $C_{10}$ alkoxy group such as a methoxy group, an ethoxy group, a propoxy group (including an isomer thereof), a butoxy group (including respective isomers thereof), a pentyloxy group (including respective isomers thereof), a hexyloxy group (including respective isomers thereof), a heptyloxy group (including respective isomers thereof), an octyloxy group (including respective isomers thereof), a nonyloxy group (including respective isomers thereof) or a decyloxy group (including respective isomers thereof), preferably a $C_1$ to $C_4$ alkoxy group, more preferably a methoxy group or a tert-butoxy group.

As "the $C_1$ to $C_{10}$ alkylthio group" which is a substituent(s) of "the $C_1$ to $C_{10}$ alkyl group having a substituent(s)" of (8), there may be mentioned, for example, a straight or branched $C_1$ to $C_{10}$ alkylthio group such as a methylthio group, an ethylthio group, a propylthio group (including an isomer thereof), a butylthio group (including respective isomers thereof), a pentylthio group (including respective isomers thereof), a hexylthio group (including respective isomers thereof), a heptylthio group (including respective isomers thereof), an octylthio group (including respective isomers thereof), a nonylthio group (including respective isomers thereof) or a decylthio group (including respective isomers thereof), preferably a $C_1$ to $C_4$ alkylthio group, more preferably a methylthio group or an ethylthio group.

As the acylamino group which is a substituent of "the $C_1$ to $C_{10}$ alkyl group having a substituent(s)" of (8), there may be mentioned, for example, a formamido group, an acetamido group, a chloroacetamido group, a benzoylamido group, a phenylacetamido group, a methoxycarbonylamino group, an ethoxycarbonylamino group, an allyloxycarbonylamino group, a tert-butoxycarbonylamino group or a benzyloxycarbonylamino group, preferably a formamido group, an acetamido group, a benzoylamido group, a methoxycarbonylamino group, a tert-butoxycarbonylamino group or a benzyloxycarbonylamino group, more preferably an acetamido group or a tert-butoxycarbonylamino group.

In the present invention, "the phenyl group which may be substituted" represented by $R^2$ in the compound (I) means a phenyl group or "a phenyl group having a substituent(s)". As the substituent(s) of "the phenyl group having a substituent(s)", there may be mentioned, for example, a benzyloxy group, the halogen atom as mentioned above, the $C_1$ to $C_6$ alkoxy group "described as the substituent of "the aryl group having a substituent(s)" of (8-2)", the acylamino group as mentioned above or the trialkylsilyloxy group as mentioned above, etc.

In the present invention, as "the $C_2$ to $C_{10}$ alkenyl group" represented by $R^2$ in the compound (I), there may be mentioned, for example, a straight or branched $C_2$ to $C_{10}$ alkenyl group such as an ethynyl group, a propenyl group (including an isomer thereof), a butenyl group (including respective isomers thereof), a pentenyl group (including respective isomers thereof), a hexenyl group (including respective isomers thereof), a heptenyl group (including respective isomers thereof), an octaneyl group (including respective isomers thereof), a nonenyl group (including respective isomers thereof) or a decenyl group (including respective isomers thereof), preferably a $C_2$ to $C_4$ alkenyl group, more preferably an ethynyl group or a propenyl group (including an isomer thereof).

Specific examples of such $R^2$ may include, for example, a hydrogen atom, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-carbomethoxyethyl group, a 3-carbomethoxypropyl group, a 4-carbomethoxybutyl group, a 1-trimethylsilyloxyethyl group, a benzyloxymethyl group, a 1-benzyloxyethyl group, a 1-benzyloxypropyl group, a 1-benzyloxybutyl group, a methoxymethyl group, a 1-tert-butoxyethyl group, a 1-ethoxyethyl group, a 1-hexyloxyethyl group, an isopropoxymethyl group, a 1-n-propoxymethyl group, a 2-methylthioethyl group, a 2-ethylthioethyl group, a methylthiomethyl group, a butylthiomethyl group, a tert-butylthiomethyl group, a benzylthiomethyl group, a 2-trifluoroethyl group, a trifluoromethyl group, a 2-chloroethyl group, a fluoromethyl group, a 1-fluorobutyl group, a 1-fluoro-1-phenylmethyl group, a 1-fluoroethyl group, a 2-acetylamidoethyl group, a 3-benzoylamidopropyl group, a 4-formylamidobutyl group, a 4-acetylamidobutyl group, a 4-chloroacetamidobutyl group, a 4-phenylacetamidobutyl group, a 4-methoxycarbonylaminobutyl group, a 4-ethoxycarbonylaminobutyl group, a 4-allyloxycarbonylaminobutyl group, a 4-tert-butyloxycarbonylaminobutyl group, a 4-benzyloxycarbonylaminobutyl group, a 4-phthaloylaminobutyl group, a benzyl group, a 4-nitrobenzyl group, a 4-cyanobenzyl group, a 4-carbomethoxybenzyl group, a 4-trimethylsilyloxybenzyl group, a 4-benzyloxybenzyl group, a 3,4-dichlorobenzyl group, a 2-fluorobenzyl group, a 4-fluorobenzyl group, a 3,4-difluorobenzyl group, a 4-methylbenzyl group, a 2-methylbenzyl group, a 2,4-di-methylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a 4-tert-butoxycarbonylaminobenzyl group, a 4-acetylamidobenzyl group, a 2-benzyloxycarbonylaminobenzyl group, a 1-phenylethyl group, a 1-(4-nitrophenyl)ethyl group, a 1-(4-bromophenyl)ethyl group, a 1-(4-fluorophenyl)ethyl group, a 1-(4-methoxyphenyl)ethyl group, a 1-(4-chlorophenyl)ethyl group, a 1-(1-naphthyl)ethyl group, a 1-(2-naphthyl)ethyl group, a diphenylmethyl group, a di(4-chlorophenyl)methyl group, a di(4-methoxyphenyl)methyl group, a trityl group, a 2-phenylethyl group, a 2-(4-benzyloxyphenyl)ethyl group, a furfuryl group, a thienylmethyl group, a thiazolylmethyl group, an isoxazolylmethyl group, an oxazolylmethyl group, a (4-N-methylimidazolyl)methyl group, a N-methylindolylmethyl group, a phenyl group, a 2-fluorophenyl group, a 4-benzyloxyphenyl group, a 4-methoxyphenyl group, a 2-chlorophenyl group, a 4-bromophenyl group, a 4-acetaminophenyl group, a 4-benzyloxycarbonylaminophenyl group, an ethynyl group, a 1-propenyl group, a 2-propenyl group, a 1-butenyl group, a 2-butenyl group, a 3-butenyl group, a 1-pentenyl group, a 2-pentenyl group, a hexenyl group, a heptenyl group, an octenyl group, a nonenyl group or a decenyl group, preferably a hydrogen atom, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-carbomethoxyethyl group, a 3-carbomethoxypropyl group, a 4-carbomethoxybutyl group, a 1-trimethylsilyloxyethyl group, a benzyloxymethyl group, a 1-benzyloxyethyl group, a 1-benzyloxypropyl group, a 1-benzyloxybutyl group, a methoxymethyl group, a 1-tert-butoxyethyl group, a 1-ethoxyethyl group, a 1-hexyloxyethyl group, an isopropoxymethyl group, a 1-n-propoxymethyl group, a 2-methylthioethyl group, a 2-ethylthioethyl group, a methylthiomethyl group, a butylthiomethyl group, a tert-butylthiomethyl group, a benzylthiomethyl group, a 2-trifluoroethyl group, a trifluoroethyl group, a 2-chloroethyl group, a fluoromethyl group, a 1-fluorobutyl group, a 1-fluoro-1-phenylmethyl group, a 1-fluoroethyl group, a 2-acetylamidoethyl group, a 3-benzoylamidopropyl group, a 4-formylamidobutyl group, a 4-acetylamidobutyl group, a 4-chloroacetamidobutyl group, a 4-phenylacetamidobutyl group, a 4-methoxycarbonylaminobutyl group, a 4-ethoxycarbonylaminobutyl group, a 4-allyloxycarbonylaminobutyl group, a 4-tert-butyloxycarbonylaminobutyl group, a 4-benzyloxycarbonylaminobutyl group, a 4-phthaloylaminobutyl group, a benzyl group, a 4-nitrobenzyl group, a 4-cyanobenzyl group, a 4-carbomethoxybenzyl group, a 4-trimethylsilyloxybenzyl group, a 4-benzyloxybenzyl group, a 3,4-difluorobenzyl group, a 4-methylbenzyl group, a 2-methylbenzyl group, a 2,4-dimethylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2-ethoxybenzyl group, a 4-isopropoxybenzyl group, a 4-tert-butoxybenzyl group, a 4-tert-butoxycarbonylaminobenzyl group, a 4-acetylamidobenzyl group, a 2-benzyloxycarbonylaminobenzyl group, a 1-phenylethyl group, a 1- (4-nitrophenyl) ethyl group, a 1-(4-bromophenyl)ethyl group, a 1-(4-fluorophenyl)ethyl group, a 1-(4- methoxyphenyl)ethyl group, a 1-(4-chlorophenyl)ethyl group, a 1-(1-naphthyl)ethyl group, a 1-(2-naphthyl)ethyl group, a diphenylmethyl group, a di(4-chlorophenyl)methyl group, a di(4-methoxyphenyl)methyl group, a trityl group, a 2-phenylethyl group, a 2-(4-benzyloxyphenyl)ethyl group, a furfuryl group, a thienylmethyl group, a thiazolylmethyl group, an isoxazolylmethyl group, an oxazolylmethyl group, a (4-N-methylimidazolyl)methyl group or a N-methylindolylmethyl group, more preferably a hydrogen atom, a methyl group, an ethyl group, a propyl group, an isopropyl group, a sec-butyl group or a tert-butyl group.

In the present invention, $R^3$ in the compound (I) represents a $C_1$ to $C_{10}$ alkyl group which may be substituted, a $C_3$ to $C_{10}$ cycloalkyl group which may be substituted, a $C_2$ to $C_{10}$ alkenyl group (provided that a 2-alkenyl group is excluded) which may be substituted or a phenyl group which may be substituted. "The $C_1$ to $C_{10}$ alkyl group which may be substituted" represented by $R^3$ in the compound (I) means (9) "a $C_1$ to $C_{10}$ alkyl group having no substituent" or (10) "a $C_1$ to $C_{10}$ alkyl group having a substituent(s)".

As "the $C_1$ to $C_{10}$ alkyl group having no substituent" of (9), there may be mentioned, for example, a straight or branched $C_1$ to $C_{10}$ alkyl group such as a methyl group, an ethyl group, a propyl group (including an isomer thereof), a butyl group (including respective isomers thereof), a pentyl group (including respective isomers thereof), a hexyl group (including respective isomers thereof), a heptyl group (including respective isomers thereof), an octyl group (including respective isomers thereof), a nonyl group (including respective isomers thereof) or a decyl group (including respective isomers thereof), preferably a $C_1$ to $C_6$ alkyl group, more preferably a methyl group, an ethyl group, a propyl group or a butyl group.

A $C_1$ to $C_{10}$ alkyl group in "the $C_1$ to $C_{10}$ alkyl group having substituent(s)" of (10) has the same meaning as in "the $C_1$ to $C_{10}$ alkyl group having no substituent" of (9). As the substituent of "the $C_1$ to $C_{10}$ alkyl group having a substituent(s)" of (10), there may be mentioned, for example, a benzyloxy group, the alkoxycarbonyl group as mentioned above, the acylamino group as mentioned above, the halogen atom as mentioned above, "the aryl group which may be substituted" "mentioned at (8-1) and (8-2)" or a $C_1$ to $C_{10}$ alkoxy group "mentioned at (2-5)".

"The cycloalkyl group which may be substituted" represented by $R^3$ in the compound (I) means (11) "a $C_3$ to $C_{10}$ cycloalkyl group having no substituent" or (12) "a $C_3$ to $C_{10}$ cycloalkyl group having a substituent(s)".

"The $C_3$ to $C_{10}$ cycloalkyl group having no substituent" of (11) has the same meaning as "the $C_3$ to $C_{10}$ cycloalkyl group having no substituent" mentioned in the above (3), and "the $C_3$ to $C_{10}$ cycloalkyl group having a substituent(s)" of (12) has the same meaning as "the $C_3$ to $C_{10}$ cycloalkyl group having a substituent(s)" mentioned in the above (4).

"The $C_2$ to $C_{10}$ alkenyl group which may be substituted (provided that a 2-alkenyl group is excluded)" represented by $R^1$ in the compound (I) means (13) "a $C_2$ to $C_{10}$ alkenyl group having no substituent (provided that a 2-alkenyl group is excluded)" or (14) "a $C_2$ to $C_{10}$ alkenyl group having a substituent(s) (provided that a 2-alkenyl group is excluded)".

As "the $C_2$ to $C_{10}$ alkenyl group having no substituent (provided that a 2-alkenyl group is excluded)" of (13), there may be mentioned, for example, a straight or branched $C_2$ to $C_{10}$ alkenyl group (provided that a 2-alkenyl group is excluded) such as an ethynyl group, a propenyl group (including an isomer thereof), a butenyl group (including respective isomers thereof), a pentenyl group (including respective isomers thereof), a hexenyl group (including respective isomers thereof), a heptenyl group (including respective isomers thereof), an octaneyl group (including respective isomers thereof), a nonenyl group (including respective isomers thereof) or a decenyl group (including respective isomers thereof), preferably a $C_3$ to $C_7$ alkenyl group (provided that a 2-alkenyl group is excluded), more preferably a 4-pentenyl group, a 3-pentenyl group or a 3-butenyl group.

When the process represented by the reaction formula (2) of the present invention as mentioned below is carried out by using the compound (II) represented by the formula (II) containing a 2-alkenyl group in the molecule as $R^3$, the compound (I) cannot be obtained.

The $C_2$ to $C_{10}$ alkenyl group of "the $C_2$ to $C_{10}$ alkenyl group having a substituent(s) (provided that a 2-alkenyl group is excluded)" of (14) has the same meaning as "the $C_2$ to $C_{10}$ alkenyl group having no substituent (provided that a 2-alkenyl group is excluded)" of (13). As the substituent(s) of "the $C_2$ to $C_{10}$ alkenyl group having a substituent(s) (provided that a 2-alkenyl group is excluded)" of (14), there may be mentioned, for example, a benzyloxy group, the alkoxycarbonyl group as mentioned above, the halogen atom as mentioned above, the acylamino group as mentioned above, "the aryl group which may be substituted" "mentioned at (8-1) and (8-2)" or a $C_3$ to $C_{10}$ alkoxy group "mentioned at (2-5)". Incidentally, the number of the substituent(s) and the position thereof are not limited.

"The phenyl group which may be substituted" represented by $R^3$ in the compound (I) means a phenyl group or "a phenyl group having a substituent(s)". As the substituent(s) of "the phenyl group having a substituent(s)", there may be mentioned, for example, a straight or branched $C_1$ to $C_6$ alkyl group such as a methyl group, an ethyl group, a propyl group (including an isomer thereof), a butyl group (including respective isomers thereof), a pentyl group (including respective isomers thereof) or a hexyl group (including respective isomers thereof); a nitro group, a benzyloxy group, the halogen atom as mentioned above; an acylamino group such as a formamido group, an acetamido group, a benzoylamido group, a methoxycarbonylamino group; or a straight or branched $C_1$ to $C_6$ alkoxy group such as a methoxy group, an ethoxy group, a propoxy group (including an isomer thereof), a butoxy group (including respective isomers thereof), a pentyloxy group (including respective isomers thereof) or a hexyloxy group (including respective isomers thereof), preferably a methyl group, an ethyl group, a propyl group (including an isomer thereof), a butyl group (including respective isomers thereof) or a halogen atom, more preferably a methyl group, an ethyl group, an isopropyl group, a tert-butyl group, a fluorine atom or a chlorine atom.

Specific examples of such R3 may include, for example, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-carbomethoxyethyl group, a 3-carbomethoxypropyl group, a 4-carbomethoxybutyl group, a 1-benzyloxyethyl group, a 3-benzyloxypropyl group, a 3-benzyloxyisobutyl group, a 2-methoxyethyl group, a 2-tert-butoxyethyl group, a 2-ethoxyethyl group, a 2-hexyloxyethyl group, a 2-isopropoxyethyl group, a 3-n-propoxypropyl group, a 2-trifluoroethyl group, a trifluoromethyl group, a 2-chloroethyl group, a fluoromethyl group, a 2-fluoromethyl group, a 1-fluorobutyl group, a 1-fluoro-1-phenylmethyl group, a 1-fluoroethyl group, a 2-bromoethyl group, a 2-acetylamidoethyl group, a 3-benzoylamidopropyl group, a 4-formylamidobutyl group, a 4-acetylamidobutyl group, a 4-chloroacetamidobutyl group, a 4-phenylacetamidobutyl group, a 4-methoxycarbonylaminobutyl group, a 4-ethoxycarbonylaminobutyl group, a 4-allyloxycarbonylaminobutyl group, a 4-tert-butyloxycarbonylaminobutyl group, a 4-benzyloxycarbonylaminobutyl group, a benzyl group, a 4-nitrobenzyl group, a 4-trimethylsilyloxyaminobutyl group, a 4-benzyloxybenzyl group, a 3,4-dichlorobenzyl group, a 2-fluorobenzyl group, a 4-fluorobenzyl group, a 3,4-difluorobenzyl group, a 4-methylbenzyl group, a 2-methylbenzyl group, a 2,4-dimethylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a 4-tert-butoxycarbonylaminobenzyl group, a 4-acetylamidobenzyl group, a 2-benzyloxycarbonylbenzyl group, a 1-phenylethyl group, a 1-(4-nitrophenyl)ethyl group, a 1-(4-bromophenyl)ethyl group, a 1-(4-fluorophenyl)ethyl group, a 1-(4-methoxyphenyl)ethyl group, a 1-(4-chlorophenyl)ethyl group, a 1-(1-naphthyl) ethyl group, a 1-(2-naphthyl)ethyl group, a diphenylmethyl group, a di(4-chlorophenyl)methyl group, a di(4-methoxyphenyl)methyl group, a trityl group, a 2-phenylethyl group, a 2-(4-benzyloxyphenyl)ethyl group, an ethynyl group, a 1-propenyl group, a 1-butenyl group, a 3-butenyl group, a 1-pentenyl group, a 3-pentenyl group, a 4-pentenyl group, a 5-hexenyl group, a 6-heptenyl group, a 7-octenyl group, a 8-nonenyl group, a 9-decenyl group, a 3-carbomethoxy-1-propenyl group, a 1-carbomethoxyethynyl group, a 2-benzyloxymethylethynyl group, a 3-chloro-4-pentenyl group, a 4-chloro-3-butenyl group, a 4-phenyl-3-butenyl group, a 5-phenyl-4-pentenyl group, a 5-benzyloxy-3-butenyl group, a 6-methoxy-3-hexenyl group, a cyclopropyl group, a cyclobutyl group, a cyclopentyl group, a cyclohexyl group, a cycloheptyl group, a cyclooctyl group, a cyclononyl group, a cyclodecyl group, a 1-carbomethoxycyclopropyl group, a 2-phenylcyclopropyl group, a 2-fluorocyclopropyl group, a 2-chlorocyclopropyl group, a 1-benzyloxymethylcyclopentyl group, a 3-cyanocyclopentyl group, a 2-acetamidocyclohexyl group, a 2-benzoylamidocyclohexyl group, a 2-methoxycarbonylaminocyclohexyl group, a 2-tert-butoxycarbonylaminocyclohexyl group, a 2-benzyloxycarbonylaminocyclohexyl group, a 2-methoxycyclohexyl group, a 2-chlorocyclohexyl group, a 2-norbornyl group, a bornyl group, a 2-adamantyl group, a N-benzosulfonyl-N-(3,5-dimethylphenyl)aminobornyl group, a 4-methylcyclohexyl group, a 2-methylcyclohexyl group, a 2,3-dimethylcyclohexyl group, a 1-carbomethoxycyclohexyl group, a 2-trimethylsiloxycyclohexyl group, a 2-benzyloxycyclohexyl group, a 4-benzyloxycyclohexyl group, a 4-tert-butylcyclohexyl group, a menthyl group, a 8-phenylmenthyl group, a phenyl group, a 2-methylphenyl group, a 4-methylphenyl group, a 4-tert-butylphenyl group, a 2,5-di-tert-butyl-4-methylphenyl group, a 2-chlorophenyl group, a 3-chlorophenyl group, a 4-chlorophenyl group, a 2-fluorophenyl group, a 4-fluorophenyl group or a 4-nitrophenyl group, preferably a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 3-butenyl group, a 3-pentenyl group, a 4-pentenyl group, a 5-hexenyl group, a 6-heptenyl group, a 7-octenyl group, a 8-nonenyl group, a 9-decenyl group, a cyclopropyl group, a cyclobutyl group, a cyclopentyl group, a cyclohexyl group, a cycloheptyl group, a cyclooctyl group, a cyclononyl group, a cyclodecyl group, a 1-carbomethoxycyclopropyl group, a 2-phenylcyclopropyl group, a 2-fluorocyclopropyl group, a 2-chlorocyclopropyl group, a 1-benzyloxymethylcyclopentyl group, a 3-cyanocyclopentyl group, a 2-norbornyl group, a bornyl group, a 2-adamantyl group, a N-benzosulfonyl-N-(3,5-dimethylphenyl) aminobornyl group, a 4-methylcyclohexyl group, a 2-methylcyclohexyl group, a 2,3-dimethylcyclohexyl group, a 1-carbomethoxycyclohexyl group, a 2-methoxycyclohexyl group, a 2-trimethylsiloxycyclohexyl group, a 2-benzyloxycyclohexyl group, a 4-benzyloxycyclohexyl group, a 4-tert-butylcyclohexyl group, a menthyl group, a 8-phenylmenthyl group, a phenyl group, a 2-methylphenyl group, a 4-methylphenyl group, a 4-tert-butylphenyl group, a 2,5-di-tert-butyl-4-methylphenyl group, a 2-chlorophenyl group, a 3-chlorophenyl group, a 4-chlorophenyl group, a 2-fluorophenyl group, a 4-fluorophenyl group or a 4-nitrophenyl group, more preferably a methyl group, an ethyl group, a n-propyl group, an isopropyl group, a 4-pentenyl group, a cyclohexyl group, a menthyl group, a 8-phenylmenthyl group or a phenyl group.

In the above-mentioned compound (I), there may be mentioned as a preferred compound including:

1) a compound wherein $R^1$ is a hydrogen atom, a $C_1$ to $C_{10}$ alkyl group which may be substituted, a $C_3$ to $C_{10}$ cycloalkyl group which may be substituted, a $C_2$ to $C_{10}$ alkenyl group which may be substituted or a phenyl group which may be substituted, 2) a compound wherein $R^1$ is a $C_1$ to $C_6$ alkyl group which may be substituted, a $C_3$ to $C_6$ cycloalkyl group which may be substituted, a $C_2$ to $C_4$ alkenyl group which is not substituted or a phenyl group which may be substituted, 3) a compound wherein $R^1$ is a $C_1$ to $C_4$ alkyl group which may be substituted, a cyclohexyl group, a $C_2$ to $C_3$ alkenyl group which may be substituted or a phenyl group which may be substituted, 4) a compound wherein $R^1$ is a $C_1$ to $C_4$ alkyl group which is not substituted, a $C_1$ to $C_4$ alkyl group which is substituted by an aryl group which may be substituted or a heteroaromatic ring group which may be substituted, or a phenyl group, 5) a compound wherein $R^1$ is a benzyl group, a 4-methylbenzyl group, a 3,4-dimethoxybenzyl group, an a 1-phenylethyl group, a diphenylmethyl group, a (1-naphthyl)-methyl group, a 1-(1-naphthyl) ethyl group, a furfuryl group, an isopropyl group, a methyl group or a phenyl group, 6) a compound wherein $R^2$ is a hydrogen atom, a $C_1$ to $C_{10}$ alkyl group which may be substituted, a phenyl group which may be substituted or a $C_2$ to $C_{10}$ alkenyl group which is not substituted, 7) a compound wherein $R^2$ is a hydrogen atom or a $C_1$ to $C_6$ alkyl group which may be substituted or a $C_2$ to $C_4$ alkenyl group which is not substituted, 8) a compound wherein $R^2$ is a hydrogen atom or a $C_1$ to $C_4$ alkyl group which may be substituted or a $C_2$ to $C_3$ alkenyl group which is not substituted, 9) a compound wherein $R^2$ is a hydrogen atom, a methyl group, an ethyl group, a propyl group or an isopropyl group, 10) a compound wherein $R^3$ is a $C_1$ to $C_{10}$ alkyl group which may be substituted, a $C_3$ to $C_{10}$ cycloalkyl group which may be substituted, a $C_2$ to $C_{10}$ alkenyl group which may be substituted (provided that a 2-alkenyl group is excluded) or a phenyl group which may be substituted, 11) a compound wherein $R^3$ is a $C_1$ to $C_6$ alkyl group which may be substituted, a $C_3$ to $C_{10}$ alkenyl group which may be substituted (provided that a 2-alkenyl group is excluded), a $C_3$ to $C_6$ cycloalkyl group which may be substituted or a phenyl group which may be substituted, 12) a compound wherein $R^3$ is a $C_1$ to $C_4$ alkyl group which may be substituted, a $C_4$ to $C_5$ alkenyl group which may be substituted (provided that a 2-alkenyl group is excluded), a cyclohexyl group which may be substituted or a phenyl group, 13) a compound wherein $R^3$ is a methyl group, an ethyl group, a propyl group, an isopropyl group, a 4-pentenyl group, a menthyl group, a 8-phenylmenthyl group or a phenyl group.

Also, a compound obtained by optionally combining $R^1$ selected from 1) to 5), $R^2$ selected from 6) to 9) and $R^3$ selected from 10) to 13) is preferred.

As the preferred compounds in the formula (I), the compounds specifically shown in the following Table 1 may be exemplified.

Incidentally, in the table, Me represents a methyl group, Et an ethyl group, Pr a propyl group, Bu a butyl group, Ph a phenyl group, Bz a benzoyl group, BOC a tert-butoxycarbonyl group, Cbz a benzyloxycarbonyl group, Bn a benzyl group and Ac an acetyl group, respectively. Also, * represents an asymmetric carbon.

TABLE 1

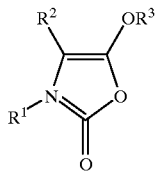

(I)

| Compound No. | $R^1$ | $R^2$ | $R^3$ |
| --- | --- | --- | --- |
| 1 | H | Me— | -i-Pr |
| 2 | Me— | Me— | -i-Pr |
| 3 | Et— | Me— | -i-Pr |
| 4 | n-Pr— | Me— | -i-Pr |
| 5 | i-Pr— | H | —Me |
| 6 | i-Bu— | H | —Me |
| 7 | sec-Bu— | H | —Me |
| 8 | tert-Bu— | H | —Me |
| 9 | n-$C_5H_{11}$— | Me— | -i-Pr |
| 10 | n-$C_6H_{13}$— | Me— | -i-Pr |
| 11 | n-$C_7H_{15}$— | Me— | -i-Pr |
| 12 | n-$C_8H_{17}$— | Me— | -i-Pr |
| 13 | n-$C_9H_{19}$— | Me— | -i-Pr |
| 14 | n-$C_{10}H_{21}$— | Me— | -i-Pr |
| 15 | NC—$CH_2CH_2$— | Me— | -i-Pr |
| 16 | $CH_3CH(CO_2Me)$— | Me— | -i-Pr |
| 17 | $Me_3SiO$—$CH_2CH_2$— | Me— | -i-Pr |
| 18 | BnO—$CH_2CH_2$— | Me— | -i-Pr |
| 19 | $CF_3CH_2$— | Me— | -i-Pr |
| 20 | $ClCH_2CH_2$— | Me— | -i-Pr |
| 21 | $PhCH_2$— | H | —Me |
| 22 | 4-$NO_2$—Ph—$CH_2$— | H | -i-Pr |
| 23 | 4-NC—Ph—$CH_2$— | Me— | -i-Pr |
| 24 | 4-$MeO_2C$—Ph—$CH_2$— | Me— | -i-Pr |
| 25 | 4-$Me_3SiO$—Ph—$CH$— | Me— | —Me |
| 26 | 4-BnO—Ph—$CH_2$— | Me— | —Me |
| 27 | 2,3-F$_2$-Ph-CH$_2$— | H | —Me |
| 28 | 4-Me—Ph—$CH_2$— | Me— | —Me |
| 29 | 2-Me—Ph—$CH_2$— | Me— | -i-Pr |
| 30 | 3,4-Cl$_2$-Ph-CH$_2$— | H | -i-Pr |

TABLE 1-continued
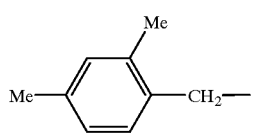
(I)
| Compound No. | R¹ | R² | R³ |
|---|---|---|---|
| 31 | 2-F—Ph—CH₂— | Me— | -i-Pr |
| 32 | 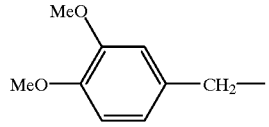 | H | —Me |
| 33 | 4-i-Pr—Ph—CH₂— | Me— | —Me |
| 34 | 4-t-Bu—Ph—CH₂— | Me— | —Me |
| 35 | 2-MeO—Ph—CH₂— | Me— | —Me |
| 36 | 4-MeO—Ph—CH₂— | Me— | —Me |
| 37 | 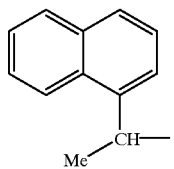 | H | —Me |
| 38 | 2-EtO—Ph—CH₂— | H | —Me |
| 39 | 4-i-PrO—Ph—CH₂— | H | —Me |
| 40 | 4-t-BuO—Ph—CH₂— | Me— | —Me |
| 41 | Ph—CH(Me)— | H | —Me |
| 42 | Ph—CH(Me)— | H | -i-Pr |
| 43 | Ph—CH(Me)— | H | —Me |
| 44 | (4-NO₂—Ph)—CH(Me)— | H | —Me |
| 45 | (4-Br—Ph)—CH(Me)— | H | —Me |
| 46 | (4-F—Ph)—CH(Me)— | Me— | —Me |
| 47 | (4-MeO—Ph)—CH(Me)— | Me— | —Me |
| 48 | (4-Cl—Ph)—CH(Me)— | Me— | -i-Pr |
| 49 | 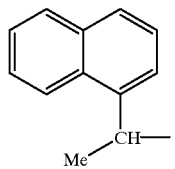 | H | —Me |
| 50 | 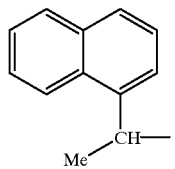 | H | -i-Pr |
| 51 | (Ph)₂CH— | Me— | —Me |
| 52 | (Ph)₂CH— | H | —Me |
| 53 | (Ph)₂CH— | H | 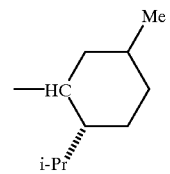 |

TABLE 1-continued
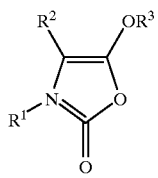
(I)
| Compound No. | R¹ | R² | R³ |
|---|---|---|---|
| 54 | (Ph)₂CH— | H | ![cyclohexyl with Me and Ph(Me)₂C substituents] |
| 55 | (4-Cl—Ph)₂CH— | H | —Me |
| 56 | (4-MeO—Ph)₂CH— | H | —Me |
| 57 | (Ph)₃C— | H | —Me |
| 58 | phenanthrenyl-CH(Me)— | H | —Me |
| 59 | anthracenyl-CH(Me)— | H | —Me |
| 60 | furan-2-yl-CH₂— | Et— | —Me |
| 61 | furan-2-yl-CH₂— | Et— | —CH₂CH₂CH₂CH=CH₂ |
| 62 | thiophen-2-yl-CH₂— | Et— | —Me |
| 63 | pyridin-2-yl-CH₂— | Me— | —Me |
| 64 | pyridin-3-yl-CH₂— | Me— | —Me |

TABLE 1-continued

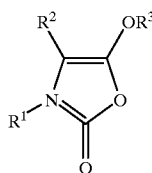

(I)

| Compound No. | R¹ | R² | R³ |
|---|---|---|---|
| 65 | (1-methylpyrrol-3-yl)-CH₂— | Me— | —Me |
| 66 | (2H-pyrrol-3-yl)-CH₂— | Me— | —Me |
| 67 | (pyrazol-1-yl)-C₂H₄— | Me— | —Me |
| 68 | (isoxazol-3-yl)-CH₂— | Me— | —Me |
| 69 | (isothiazol-3-yl)-CH₂— | Me— | —Me |
| 70 | MeOCH₂CH₂— | Me— | -i-Pr— |
| 71 | EtOCH₂CH₂— | Me— | -i-Pr |
| 72 | n-PrOCH₂CH₂— | Me— | -i-Pr |
| 73 | i-PrOCH₂CH₂— | Me— | -i-Pr |
| 74 | n-BuOCH₂CH₂— | Me— | —Me |
| 75 | sec-BuOCH₂CH₂— | Et— | —Me |
| 76 | t-BuOCH₂CH₂— | Et— | —Me |
| 77 | n-C₆H₁₃OCH₂CH₂— | Me— | —Me |
| 78 | CH₃CH₂CH(OMe)CH₂— | Me— | -i-Pr |
| 79 | t-BuOCH₂C(Me)₂— | Me— | -i-Pr |
| 80 | n-C₇H₁₅OCH₂CH₂— | Me— | -i-Pr |
| 81 | n-C₈H₁₇OCH₂CH₂— | Me— | -i-Pr |
| 82 | n-C₉H₁₉OCH₂CH₂— | Me— | -i-Pr |
| 83 | MeOC₂H₄OCH₂CH₂— | Me— | -i-Pr |
| 84 | BnOCH₂OCH₂CH₂— | Me— | -i-Pr |
| 85 | MeOC₂H₄OCH₂OCH₂CH₂— | Me— | —Me |
| 86 | EtOCH₂OCH₂CH₂— | Et— | —Me |
| 87 | PhOCH₂OCH₂CH₂— | Et— | —Me |
| 88 | HCONH—CH₂CH₂— | Me— | —Me |
| 89 | AcNH—CH₂CH₂— | Me— | —Me |
| 90 | ClCH₂CONH—CH₂CH₂— | Me— | —Me |
| 91 | BzNH—CH₂CH₂— | Me— | —Me |
| 92 | PhCH₂CONH—CH₂CH₂— | Me— | —Me |
| 93 | MeO₂CNH—CH₂CH₂— | Me— | —Me |
| 94 | EtO₂CNH—CH₂CH₂— | Me— | —Me |
| 95 | CH₂=CHCH₂O₂CNH—CH₂CH₂— | Me— | —Me |
| 96 | BocNH—CH₂CH₂— | Me— | —Me |
| 97 | CbzNH—CH₂CH₂— | Me— | —Me |
| 98 | CH₂=CH— | Me— | —Me |

TABLE 1-continued

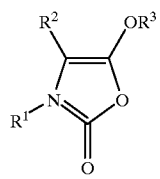

(I)

| Compound No. | R¹ | R² | R³ |
|---|---|---|---|
| 99 | CH₂=CHCH₂— | Me— | —Me |
| 100 | CH₂=CHCH₂CH₂— | Et— | —Me |
| 101 | CH₂=CHCH₂CH₂CH₂— | Et— | —Me |
| 102 | CH₃CH₂CH₂CH=CHCH₂— | Me— | —Me |
| 103 | CH₃CH₂CH₂CH₂CH=CHCH₂— | Me— | —Me |
| 104 | CH₃(CH₂)₄CH=CHCH₂— | Me— | —Me |
| 105 | CH₃(CH₂)₄CH=CHCH₂CH₂— | Me— | —Me |
| 106 | CH₃(CH₂)₄CH=CHCH₂CH₂CH₂— | Me— | —Me |
| 107 | NC—CH=CH— | Me— | -i-Pr |
| 108 | CH₂=CH—CH(CO₂Me)— | Me— | -i-Pr |
| 109 | CH₂=CH—CH(SiMe₃)— | Me— | -i-Pr |
| 110 | CH₂=CH—CH(CH₂OBn)— | Me— | —Me |
| 111 | Ph—CH=CH—CH₂— | Et— | —Me |
| 112 | CH₂=CH—CH(CH₂OMe)— | Et— | —Me |
| 113 | CH₂=CH—CH(CH₂OEt)— | Me— | —Me |
| 114 | cyclopropyl-CH₂— | Me— | —Me |
| 115 | cyclobutyl-CH₂— | H | —Me |
| 116 | cyclopentyl-CH₂— | H | —Me |
| 117 | cyclohexyl-CH₂— | H | —Me |
| 118 | cycloheptyl-CH₂— | H | —Me |
| 119 | cyclooctyl-CH₂— | H | —Me |
| 120 | cyclononyl-CH₂— | H | —Me |
| 121 | cyclodecyl-CH₂— | H | —Me |
| 122 | 1-(CO₂Me)-1-methylcyclopropyl— | H | —Me |

TABLE 1-continued (I)

| Compound No. | R¹ | R² | R³ |
|---|---|---|---|
| 123 | Ph-cyclopropyl-Me | H | —Me |
| 124 | F-cyclopropyl-Me | H | —Me |
| 125 | Cl-cyclopropyl-Me | H | —Me |
| 126 | 2-methyl-1-(benzyloxy)cyclopentyl | H | —Me |
| 127 | 1-methyl-1-cyanocyclopentyl | H | —Me |
| 128 | norbornyl | H | —Me |
| 129 | 2,6,6-trimethylbicyclo[3.1.1]heptyl | H | —Me |
| 130 | 1-adamantyl | H | —Me |
| 131 | 2,5-dimethylcyclohexyl | H | —Me |
| 132 | 1,2-dimethylcyclohexyl | H | —Me |

TABLE 1-continued

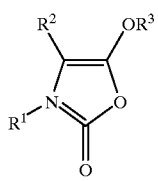

(I)

| Compound No. | R¹ | R² | R³ |
|---|---|---|---|
| 133 | (2,3-dimethylcyclohexyl) | H | —Me |
| 134 | (1-methyl-1-(CO₂Me)cyclohexyl) | H | —Me |
| 135 | (2-methyl-1-methoxycyclohexyl) | H | —Me |
| 136 | (2-methyl-1-OSiMe₃-cyclohexyl) | H | —Me |
| 137 | (2-methyl-1-OBn-cyclohexyl) | H | —Me |
| 138 | (4-methyl-1-OBn-cyclohexyl) | H | —Me |
| 139 | (4-methyl-1-Ot-Bu-cyclohexyl) | H | —Me |
| 140 | (4-methyl-2-i-Pr-cyclohexyl) | H | —Me |
| 141 | PhCH²— | n-Pr— | —Me |
| 142 | PhCH₂— | n-Bu— | —Me |
| 143 | PhCH(Me)— | i-Bu— | —Me |
| 144 | PhCH(Me)— | sec-Bu— | —Et |
| 145 | PhCH(Me)— | tert-Bu— | —Et |
| 146 | Ph₂CH— | n-C₅H₁₁— | —Me |
| 147 | Ph₂CH— | n-C₅H₁₁— | —Me |
| 148 | Ph₂CH— | n-C₆H₁₃— | -n-Bu |
| 149 | Ph₂CH— | n-C₇H₁₅— | —Me |
| 150 | Ph₂CH— | n-C₈H₁₇— | —Me |

TABLE 1-continued

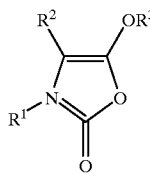

(I)

| Compound No. | R¹ | R² | R³ |
|---|---|---|---|
| 151 | Ph₂CH— | n-C₉H₁₉— | —Me |
| 152 | Ph₂CH— | n-C₁₀H₂₁— | —Et |
| 153 | PhCH₂— | MeO₂C—CH₂CH₂— | —Et |
| 154 | PhCH₂— | MeO₂C—CH₂CH₂CH₂— | —Et |
| 155 | PhCH₂— | MeO₂C—CH₂CH₂CH₂CH₂— | —Et |
| 156 | PhCH(Me)— | CH₃CH(OSiMe₃)— | -n-Bu |
| 157 | (1-naphthyl)CH(Me)— | BnO—CH₂— | —Me |
| 158 | PhCH(Me)— | CH₃CH(OBn)— | —Me |
| 159 | PhCH(Me)— | CH₃CH₂CH(OBn)— | —Me |
| 160 | PhCH(Me)— | CH₃CH₂CH₂CH(OBn)— | —Et |
| 161 | PhCH(Me)— | MeO—CH₂— | —Et |
| 162 | PhCH(Me)— | CH₃CH(O-t-Bu)— | —Me |
| 163 | PhCH(Me)— | CH₃CH(OEt)— | —Me |
| 164 | PhCH(Me)— | CH₃CH(O-n-C₆H₁₃)— | —Me |
| 165 | PhCH₂— | i-PrOCH₂— | —Me |
| 166 | PhCH₂— | n-PrOCH₂— | —Me |
| 167 | (1-naphthyl)CH(Me)— | MeSCH₂CH₂— | —Me |
| 168 | PhCH(Me)— | EtSCH₂CH₂— | —Et |
| 169 | PhCH(Me)— | MeSCH₂— | —Et |
| 170 | Ph₂CH— | n-BuSCH₂— | —Me |
| 171 | PhCH₂— | tert-BuSCH₂— | —Me |
| 172 | Ph₂CH— | BnSCH₂— | —Me |
| 173 | PhCH(Me)— | CF₃CH₂— | —Me |
| 174 | PhCH(Me)— | CF₃— | —Me |
| 175 | Ph₂CH— | ClCH₂CH₂— | —Me |
| 176 | Ph₂CH— | FCH₂— | —Et |
| 177 | PhCH₂— | CH₃CH₂CH₂CHF— | —Et |
| 178 | PhCH₂— | PhCHF— | —Et |
| 179 | PhCH₂— | CH₃CHF— | —Et |
| 180 | PhCH(Me)— | AcNHCH₂CH₂— | —Me |
| 181 | PhCH(Me)— | BzNHCH₂CH₂— | —Me |
| 182 | PhCH(Me)— | HCONHCH₂CH₂CH₂CH₂— | —Me |
| 183 | PhCH(Me)— | AcNHCH₂CH₂CH₂CH₂— | —Me |
| 184 | PhCH(Me)— | ClCH₂CONHCH₂CH₂CH₂CH₂— | —Me |
| 185 | PhCH(Me)— | PhCH₂CONHCH₂CH₂CH₂CH₂— | —Me |
| 186 | PhCH(Me)— | MeO₂CNHCH₂CH₂CH₂CH₂— | —Me |
| 187 | PhCH(Me)— | EtO₂CNHCH₂CH₂CH₂CH₂— | —Me |
| 188 | PhCH(Me)— | CH₂=CHCH₂O₂CNHCH₂CH₂CH₂CH₂— | —Me |
| 189 | PhCH₂— | BocNHCH₂CH₂CH₂CH₂— | —Me |
| 190 | Ph₂CH— | CbzNHCH₂CH₂CH₂CH₂— | —Me |
| 191 | (1-naphthyl)CH(Me)— | phthalimido-CH₂CH₂CH₂CH₂— | —Me |

TABLE 1-continued

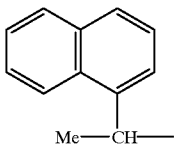

(I)

| Compound No. | R¹ | R² | R³ |
|---|---|---|---|
| 192 | PhCH(Me)— | PhCH₂— | —Me |
| 193 | PhCH(Me)— | 4-NO₂—Ph—CH₂— | —Me |
| 194 | Ph₂CH— | 4-NC—Ph—CH₂— | —Me |
| 195 | PhCH₂— | 4-MeO₂C—Ph—CH₂— | —Me |
| 196 | Ph₂CH— | 4-Me₃SiO—Ph—CH₂— | —Me |
| 197 | PhCH(Me)— | 4-BnO—Ph—CH₂— | —Me |
| 198 | 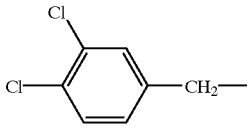 | 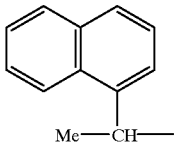 | —Me |
| 199 | Ph(Me)CH— | 2-F—Ph—CH₂— | —Me |
| 200 | PhCH₂— | 4-F—Ph—CH₂— | —Me |
| 201 | 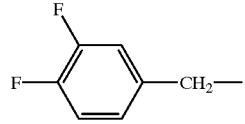 | 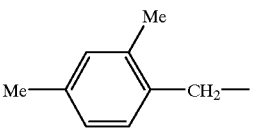 | —Me |
| 202 | PhCH₂— | 4-Me—Ph—CH₂— | —Me |
| 203 | PhCH₂— | 2-Me—Ph—CH₂— | —Et |
| 204 | PhCH(Me)— | 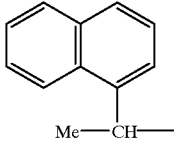 | —Me |
| 205 | PhCH(Me)— | 4-i-Pr—Ph—CH₂— | —Me |
| 206 | PhCH(Me)— | 4-t-Bu—Ph—CH₂— | —Me |
| 207 | Ph(Me)CH— | 2-MeO—Ph—CH₂— | —Me |
| 208 | PhCH₂— | 3-MeO—Ph—CH₂— | —Me |
| 209 | Ph(Me)CH— | 4-MeO—Ph—CH₂— | —Me |
| 210 | 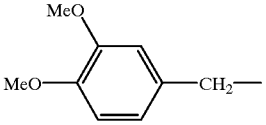 | 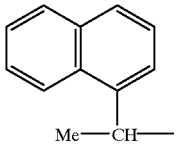 | —Me |
| 211 | 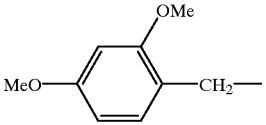 | | —Me |
| 212 | PhCH₂— | 2-EtO—Ph—CH₂— | —Me |
| 213 | PhCH₂— | 4-i-PrO—Ph—CH₂— | —Me |
| 214 | PhCH₂— | 4-t-BuO—Ph—CH₂— | —Me |
| 215 | PhCH₂— | 4-BocNH—Ph—CH₂— | —Me |
| 216 | Ph(Me)CH— | 4-AcNH—Ph—CH₂— | —Me |

TABLE 1-continued

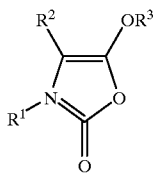
(I)

| Compound No. | R¹ | R² | R³ |
|---|---|---|---|
| 217 | PhCH₂— | 2-CbzNH—Ph—CH₂— | —Me |
| 218 | PhCH₂— | Ph—CH(Me)— | —Me |
| 219 | PhCH₂— | (4-NO₂—Ph)—CH(Me)— | —Me |
| 220 | PhCH₂— | (4-Br—Ph)—CH(Me)— | —Me |
| 221 | PhCH₂— | (4-F—Ph)—CH(Me)— | —Me |
| 222 | PhCH₂— | (4-MeO—Ph)—CH(Me)— | —Me |
| 223 | PhCH₂— | (4-Cl—Ph)—CH(Me)— | —Me |
| 224 | 1-naphthyl-CH(Me)— | 1-naphthyl-CH(Me)— | —Me |
| 225 | PhCH₂— | 2-naphthyl-CH(Me)— | —Me |
| 226 | PhCH₂— | Ph₂CH— | —Me |
| 227 | PhCH₂— | (4-Cl—Ph)₂CH— | —Me |
| 228 | PhCH₂— | (4-MeO—Ph)₂CH— | —Me |
| 229 | PhCH₂— | Ph₃C— | —Me |
| 230 | Ph(Me)CH— | Ph—CH₂CH₂— | —Me |
| 231 | Ph(Me)CH— | (4-BnO—Ph)—CH₂CH₂— | —Me |
| 232 | PhCH₂— | (2-furyl)-CH₂— | —Me |
| 233 | PhCH₂— | (2-thienyl)-CH₂— | —Me |
| 234 | 1-naphthyl-CH(Me)— | (5-oxazolyl)-CH₂— | —Me |
| 235 | PhCH₂— | (3-isoxazolyl)-CH₂— | —Me |
| 236 | PhCH₂— | (5-thiazolyl)-CH₂— | —Me |

TABLE 1-continued

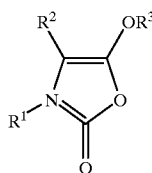

(I)

| Compound No. | R¹ | R² | R³ |
|---|---|---|---|
| 237 | PhCH₂— | CH₂— (1-methylimidazol-5-yl) | —Me |
| 238 | 1-(Me—CH—)naphthyl | CH₂— (1-methylindol-3-yl) | —Me |
| 239 | PhCH₂— | Ph— | —Me |
| 240 | PhCH₂— | 2-F—Ph— | —Me |
| 241 | PhCH₂— | 4-BnO—Ph— | —Me |
| 242 | PhCH₂— | 4-MeO—Ph— | —Me |
| 243 | 1-(Me—CH—)naphthyl | 2-Cl—Ph— | —Me |
| 244 | Ph(Me)CH— | 4-Br—Ph— | —Me |
| 245 | PhCH₂— | 4-AcNH—Ph— | —Me |
| 246 | PhCH₂— | 4-CbzNH—Ph— | —Me |
| 247 | PhCH₂— | CH₂=CH— | —Me |
| 248 | Ph(Me)CH— | CH₃CH=CH— | —Me |
| 249 | PhCH₂— | CH₂=CH—CH₂— | —Me |
| 250 | Ph(Me)CH— | CH₃CH₂CH=CH— | —Me |
| 251 | 1-(Me—CH—)naphthyl | CH₃CH=CH—CH₂— | —Me |
| 252 | PhCH₂— | CH₂=CH—CH₂CH₂— | —Me |
| 253 | PhCH₂— | CH₃CH₂CH₂CH=CH— | —Me |
| 254 | PhCH₂— | CH₃CH₂CH=CH—CH₂— | —Me |
| 255 | PhCH₂— | CH₃CH₂CH₂CH=CH—CH₂— | —Me |
| 256 | PhCH₂— | CH₃CH₂CH₂CH₂CH=CH—CH₂— | —Me |
| 257 | PhCH₂— | CH₃CH₂CH₂CH₂CH₂CH=CH—CH₂— | —Me |
| 258 | PhCH₂— | C₆H₁₃CH=CH—CH₂— | —Me |
| 259 | PhCH₂— | C₇H₁₅CH=CH—CH₂— | —Me |
| 260 | PhCH₂— | Me— | -n-Pr |
| 261 | PhCH₂— | Me— | -i-Bu |
| 262 | PhCH(Me)— | Me— | -sec-Bu |
| 263 | PhCH(Me)— | H | -tert-Bu |
| 264 | PhCH(Me)— | H | -n-C₅H₁₁ |
| 265 | Ph₂CH— | H | -n-C₆H₁₃ |
| 266 | Ph₂CH— | H | -n-C₇H₁₅ |
| 267 | Ph₂CH— | H | -n-C₈H₁₇ |
| 268 | Ph₂CH— | H | -n-C₉H₁₉ |
| 269 | Ph₂CH— | H | -n-C₁₀H₂₁ |
| 270 | Ph₂CH— | H | —CH₂CH₂—CO₂Me |

TABLE 1-continued

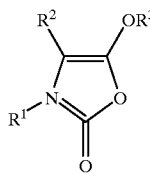

(I)

| Compound No. | R[1] | R[2] | R[3] |
|---|---|---|---|
| 271 | Ph₂CH— | H | —CH₂CH₂CH₂—CO₂Me |
| 272 | PhCH₂— | Me— | —CH₂CH₂CH₂CH₂—CO₂Me |
| 273 | PhCH₂— | Me— | —CH(OBn)CH₃ |
| 274 | PhCH₂— | Et— | —CH₂CH₂CH₂—OBn |
| 275 | PhCH(Me)— | H | —CH₂CH(CH₃)CH₂—OBn |
| 276 | PhCH(Me)— | H | —CH₂CH₂—OMe |
| 277 | PhCH(Me)— | H | —CH₂CH₂—O-t-Bu |
| 278 | 1-Naphthyl-CH(Me)— | H | —CH₂CH₂—OEt |
| 279 | PhCH(Me)— | H | —CH₂CH₂—O-n-C₆H₁₃ |
| 280 | PhCH(Me)— | H | —CH₂CH₂—O-i-Pr |
| 281 | PhCH(Me)— | H | —CH₂CH₂CH₂—O-n-Pr |
| 282 | PhCH(Me)— | H | —CH₂CF₃ |
| 283 | PhCH(Me)— | H | —CF₃ |
| 284 | PhCH₂— | Me— | —CH₂CH₂F |
| 285 | PhCH₂— | Me— | —CHFCH₂CH₃ |
| 286 | PhCH(Me)— | Me— | —CHFPh |
| 287 | PhCH(Me)— | H | —CHFCH₃ |
| 288 | PhCH(Me)— | H | —CH₂CH₂Br |
| 289 | 1-Naphthyl-CH(Me)— | H | —CH₂CH₂NHAc |
| 290 | Ph₂CH— | H | —CH₂CH₂CH₂NHBz |
| 291 | Ph₂CH— | H | —CH₂CH₂CH₂CH₂NHCHO |
| 292 | Ph₂CH— | H | —CH₂CH₂CH₂CH₂NHAc |
| 293 | Ph₂CH— | H | —CH₂CH₂CH₂CH₂NHCOCH₂Cl |
| 294 | Ph₂CH— | H | —CH₂CH₂CH₂CH₂NHCOCH₂Ph |
| 295 | Ph₂CH— | H | —CH₂CH₂CH₂CH₂NHCO₂Me |
| 296 | PhCH₂— | Me— | —CH₂CH₂CH₂CH₂NHCO₂Et |
| 297 | PhCH₂— | Me— | —CH₂CH₂CH₂CH₂NHCO₂CH₂CH=CH₂ |
| 298 | 1-Naphthyl-CH(Me)— | H | —CH₂CH₂CH₂CH₂NHBoc |
| 299 | PhCH(Me)— | H | —CH₂CH₂CH₂CH₂NHCbz |
| 300 | 1-Naphthyl-CH(Me)— | H | —CH₂Ph |
| 301 | PhCH(Me)— | H | —CH₂(4-NO₂—Ph) |
| 302 | PhCH(Me)— | H | —CH₂(4-Me₃SiO—Ph) |

TABLE 1-continued
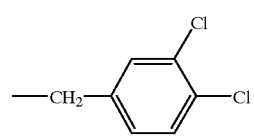
(I)
| Compound No. | R¹ | R² | R³ |
|---|---|---|---|
| 303 | PhCH(Me)— | H | —CH₂(4-BnO—Ph) |
| 304 | PhCH₂— | Me— | 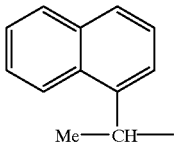 |
| 305 | PhCH₂— | Me— | —CH₂(2-F—Ph) |
| 306 | PhCH(Me)— | Me— | —CH₂(4-F—Ph) |
| 307 | 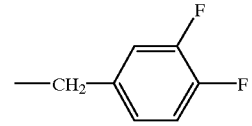 | H | 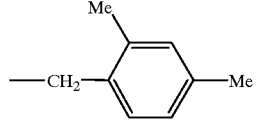 |
| 308 | PhCH(Me)— | H | —CH₂(4-MeO—Ph) |
| 309 | PhCH₂— | Me— | —CH₂(2-Me—Ph) |
| 310 | Ph₂CH— | H | 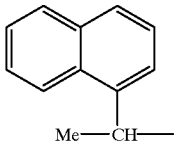 |
| 311 | PhCH(Me)— | H | —CH₂(4-i-Pr—Ph) |
| 312 | PhCH(Me)— | H | —CH₂(4-t-Bu—Ph) |
| 313 | Ph₂CH— | H | —CH₂(2-MeO—Ph) |
| 314 | Ph₂CH— | H | —CH₂(3-MeO—Ph) |
| 315 | PhCH(Me)— | H | —CH₂(4-MeO—Ph) |
| 316 | 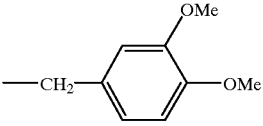 | H | 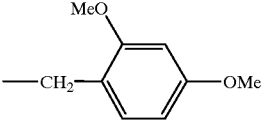 |
| 317 | PhCH₂— | Me— | 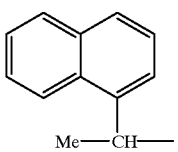 |
| 318 | PhCH₂— | Me— | —CH₂(2-EtO—Ph) |
| 319 | PhCH₂— | Me— | —CH₂(4-i-PrO—Ph) |
| 320 | PhCH(Me)— | H | —CH₂(4-t-BuO—Ph) |
| 321 |  | H | —CH₂(4-BocNH—Ph) |

TABLE 1-continued

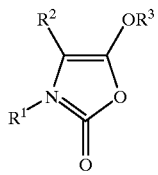

(I)

| Compound No. | R¹ | R² | R³ |
|---|---|---|---|
| 322 | PhCH(Me)— | H | —CH²(2-CbzNH—Ph) |
| 323 | PhCH₂— | Me— | PhCH(Me)— |
| 324 | Ph₂CH— | H | (4-NO₂—Ph)CH(Me)— |
| 325 | PhCH(Me)— | H | (4-Br—Ph)CH(Me)— |
| 326 | PhCH(Me)— | H | (4-F—Ph)CH(Me)— |
| 327 | Ph₂CH— | H | (4-MeO—Ph)CH(Me)— |
| 328 | Ph₂CH— | H | (4-Cl—Ph)CH(Me)— |
| 329 | PhCH(Me)— | H | (1-naphthyl)CH(Me)— |
| 330 | (1-naphthyl)CH(Me)— | H | (2-naphthyl)CH(Me)— |
| 331 | PhCH₂— | Me— | Ph₂CH— |
| 332 | PhCH(Me)— | H | (4-Cl—Ph)₂CH— |
| 333 | PhCH(Me)— | H | (4-MeO—Ph)₂CH— |
| 334 | PhCH(Me)— | H | Ph₃C— |
| 335 | PhCH(Me)— | H | Ph—CH₂CH₂— |
| 336 | Ph₂CH— | Me | (4-BnO—Ph)—CH₂CH₂— |
| 337 | Ph₂CH— | Me— | —CH=CH₂ |
| 338 | Ph₂CH— | Me— | —CH=CHCH₃ |
| 339 | PhCH(Me)— | H | —CH=CHCH₂CH₃ |
| 340 | (1-naphthyl)CH(Me)— | H | —CH₂CH₂CH=CH₂ |
| 341 | PhCH(Me)— | H | —CH=CHCH₂CH₂CH₃ |
| 342 | PhCH₂— | Me— | —CH₂CH₂CH=CHCH₃ |
| 343 | Ph₂CH— | H | —CH₂CH₂CH₂CH=CH₂ |
| 344 | PhCH(Me)— | Me— | —CH₂CH₂CH₂CH₂CH=CH₂ |
| 345 | PhCH(Me)— | H | —CH₂CH₂CH₂CH₂CH₂CH=CH₂ |
| 346 | Ph₂CH— | Me— | —CH₂CH₂CH₂CH₂CH₂CH₂CH=CH₂ |
| 347 | Ph₂CH— | H | —C₇H₁₄—CH=CH₂ |
| 348 | (1-naphthyl)CH(Me)— | H | —C₈H₁₆—CH=CH₂ |

TABLE 1-continued

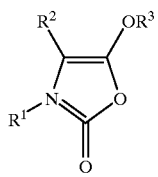

(I)

| Compound No. | R¹ | R² | R³ |
|---|---|---|---|
| 349 | 1-(Me-CH)-naphthyl | H | —CH=CH—CH$_2$CO$_2$Me |
| 350 | Ph$_2$CH— | H | —C(CO$_2$Me)=CH$_2$ |
| 351 | PhCH(Me)— | H | —CH=CH—CH$_2$(OBn) |
| 352 | PhCH(Me)— | H | —CH$_2$CH$_2$CH(Cl)CH=CH$_2$ |
| 353 | PhCH(Me)— | Me— | —CH$_2$CH$_2$CH=CHCl |
| 354 | PhCH(Me)— | H | —CH$_2$CH$_2$CH=CH—Ph |
| 355 | Ph$_2$CH— | Me— | —CH$_2$CH$_2$CH$_2$CH=CH—Ph |
| 356 | PhCH$_2$— | H | —CH$_2$CH$_2$CH=CH(OBn) |
| 357 | PhCH(Me)— | H | —CH$_2$CH$_2$CH=CHCH$_2$CH$_2$(OMe) |
| 358 | PhCH(Me)— | H | cyclopropyl |
| 359 | 1-(Me-CH)-naphthyl | H | cyclobutyl |
| 360 | i-Pr— | Me— | cyclopentyl |
| 361 | i-Pr— | Me— | cyclohexyl |
| 362 | Ph$_2$CH— | H | cycloheptyl |
| 363 | PhCH(Me)— | Me— | cyclooctyl |
| 364 | PhCH(Me)— | H | cyclononyl |

TABLE 1-continued
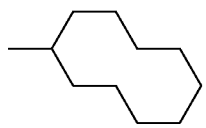
(I)
| Compound No. | R¹ | R² | R³ |
|---|---|---|---|
| 365 | Ph²CH— | Me— |  |
| 366 | Ph₂CH— | H |  |
| 367 | Ph₂CH— | Me | 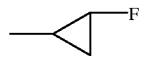 |
| 368 | PhCH(Me)— | H |  |
| 369 | PhCH(Me)— | Me— | 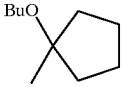 |
| 370 | PhCH(Me)— | Me— | 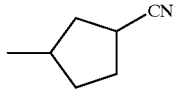 |
| 371 | PhCH(Me)— | H | 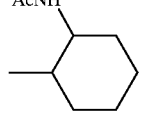 |
| 372 | PhCH₂— | H | 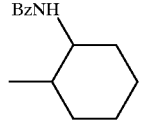 |
| 373 | PhCH(Me)— | H | 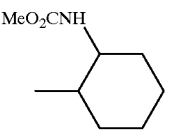 |
| 374 | PhCH(Me)— | H | 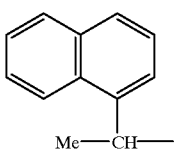 |
| 375 | 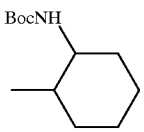 | H | |

TABLE 1-continued
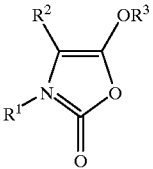
(I)
| Compound No. | R¹ | R² | R³ |
|---|---|---|---|
| 376 | PhCH(Me)— | Me— | 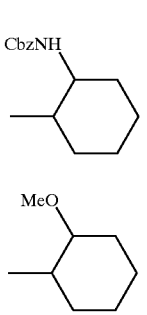 (CbzNH-cyclohexyl) |
| 377 | PhCH(Me)— | Me— | 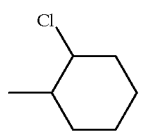 (MeO-cyclohexyl) |
| 378 | PhCH(Me)— | H | 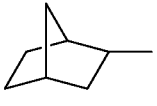 (Cl-cyclohexyl) |
| 379 | PhCH(Me)— | Me— | 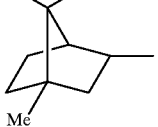 (norbornyl) |
| 380 | PhCH(Me)— | H | 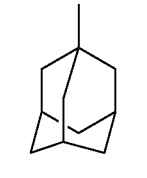 |
| 381 | PhCH(Me)— | H | 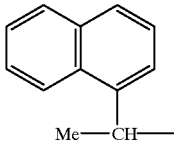 (adamantyl) |
| 382 | 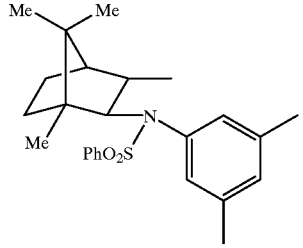 Me—CH— (naphthyl) | H | 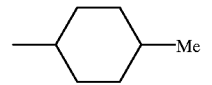 |
| 383 | PhCH(Me)— | H | (4-methylcyclohexyl)-Me |

TABLE 1-continued (I)

| Compound No. | R¹ | R² | R³ |
|---|---|---|---|
| 384 | PhCH(Me)— | H | 2-methylcyclohexyl with Me |
| 385 | 1-(naphthalen-1-yl)ethyl [Me-CH- attached to naphthalene] | H | 2,3-dimethyl-substituted cyclohexyl (trimethylcyclohexyl) |
| 386 | PhCH(Me)— | H | 1-methyl-1-(methoxycarbonyl)cyclohexyl (MeO₂C) |
| 387 | PhCH(Me)— | Me— | 2-methylcyclohexyl-O-SiMe₂ |
| 388 | PhCH(Me)— | H | 2-methylcyclohexyl-OBn |
| 389 | PhCH(Me)— | Me— | 4-methylcyclohexyl-OBu |
| 390 | PhCH(Me)— | H | 4-methyl-4-t-Bu-cyclohexyl |
| 391 | PhCH(Me)— | Me— | cyclohexyl |
| 392 | 1-(naphthalen-1-yl)ethyl [Me-CH- attached to naphthalene] | H | cyclohexyl |
| 393 | i-Pr— | Me— | —Me |
| 394 | i-Pr— | Me— | —Et |

TABLE 1-continued

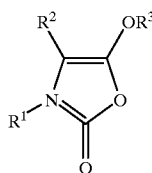

(I)

| Compound No. | $R^1$ | $R^2$ | $R^3$ |
|---|---|---|---|
| 395 | PhCH$_2$— | H | 4-Me-2-(i-Pr)-cyclohexyl |
| 396 | PhCH(Me)— | Me— | —Me |
| 397 | PhCH(Me)— | H | —Ph |
| 398 | Ph$_2$CH— | H | —Ph |
| 399 | PhCH$_2$— | H | —Me |
| 400 | 1-naphthyl-CH— | H | —Me |
| 401 | PhCH(Me)— | H | 4-Me-2-(i-Pr)-cyclohexyl |
| 402 | Ph— | Me— | —Me |
| 403 | Ph— | H | —Me |

In the above table, preferred are Compounds Nos. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 260, 261, 262, 263, 264, 265, 266, 267, 268, 269, 340, 341, 342, 343, 344, 345, 346, 347, 348, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402 and 403, more preferably Compounds Nos. 2, 3, 4, 5, 6, 7, 8, 9, 10, 11, 12, 13, 14, 21, 22, 26, 27, 28, 29, 30, 31, 32, 33, 34, 35, 36, 37,. 38, 39, 40, 41, 42, 43, 44, 45, 46, 47, 48, 49, 50, 51, 52, 53, 54, 55, 56, 57, 60, 61, 62, 63, 64, 68, 141, 142, 143, 144, 145, 146, 147, 148, 149, 150, 151, 152, 260, 261, 262, 263, 264, 265, 266, 267, 268, 269, 340, 342, 343, 358, 359, 360, 361, 362, 363, 364, 365, 379, 380, 381, 383, 384, 385, 309, 391, 392, 393, 394, 395, 396, 397, 398, 399, 400, 401, 402 and 403, particularly preferably Compound No. 5: 3-isopropyl-5-methoxy-2(3H)-oxazolone,
Compound No. 21: 3-benzyl-5-methoxy-2(3H)-oxazolone,
Compound No. 28: 3-(4-methylbenzyl)-4-methyl-5-methoxy-2 (3H)-oxazolone,
Compound No. 37: 3-(3,4-dimethoxybenzyl)-5-methoxy-2 (3H)-oxazolone,
Compound No. 41: 3-(1-phenylethyl)-5-methoxy-2(3H)-oxazolone,
Compound No. 42: 3-((S)-1-phenylethyl)-5-isopropoxy-2 (3H)-oxazolone,
Compound No. 43: 3-((R)-1-phenylethyl)-5-methoxy-2 (3H)-oxazolone,
Compound No. 49: 3-((R)-1-(1-naphthyl)ethyl-5-methoxy-2(3H)-oxazolone,
Compound No. 50: 3-((R)-1-(1-naphthyl)ethyl)-5-isopropoxy-2(3H)-oxazolone,
Compound No. 51: 3-diphenylmethyl-4-methyl-5-methoxy-2(3H)-oxazolone,
Compound No. 52: 3-diphenylmethyl-5-methoxy-2(3H)-oxazolone,
Compound No. 53: 3-diphenylmethyl-5-((l)-menthyloxy)-2 (3H)-oxazolone, Compound No. 54: 3-diphenylmethyl-5-((1S,2S,5R)-5-methyl-2-(1-methyl-1-phenylethyl)cyclohexyloxy)-2(3H)-oxazolone, Compound No. 60: 3-furfuryl-4-ethyl-5-methoxy-2(3H)-oxazolone, Compound No. 61: 3-furfuryl-4-ethyl-5-(4-pentenyl)oxy-2(3H)-oxazolone, Compound No. 361: 3-isopropyl-4-methyl-5-cyclohexyloxy-2(3H)-oxazolone, Compound No. 393: 3-isopropyl-4-methyl-5-methoxy-2(3H)-oxazolone, Compound No. 394: 3-isopropyl-4-methyl-5-ethoxy-2(3H)-oxazolone, Compound No. 395: 3-benzyl-5-(l)-menthyloxy)-2 (3H)-oxazolone, Compound No. 396: 3-((R)-1-phenylethyl)-4-methyl-5-methoxy-2(3H)-oxazolone, Compound No. 397: 3-((S)-1-phenylethyl)-5-phenoxy-2(3H)-oxazolone, Compound No. 399: 3-benzyl-4-methyl-5-methoxy-2(3H)-oxazolone, Compound No. 400: 3-(1-naphthyl)methyl-5-methoxy-2(3H)-oxazolone, Compound No. 401: 3-( (R)-1-phenylethyl)-5-((l)-menthyloxy)-2(3H)-oxazolone, 3-((S)-1-phenylethyl)-5-((l)-menthyloxy)-2(3H)-oxazolone, or Compound No. 402: 3-phenyl-4-methyl-5-methoxy-2(3H)-oxazolone.

The 5-alkoxy-2(3H)-oxazolone (hereinafter also referred to as Compound (I)) represented by the formula (I) of the present invention can be prepared according to the method of Reaction scheme (2) mentioned below.

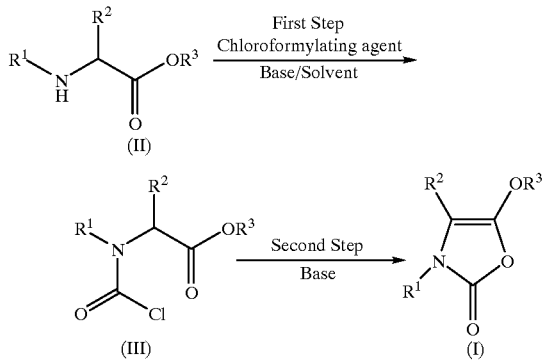

wherein $R^1$, $R^2$ and $R^3$ have the same meanings as defined above.

The first step is a process for producing a compound represented by the formula (III) (hereinafter also referred to as Compound (III)) and can be accomplished by reacting a N-substituted-a-amino acid ester (hereinafter also referred to as Compound (II)) with a chlorocarbonylating agent in the presence of a base (1) in a solvent.

The chlorocarbonylating agent to be used may be mentioned, for example, phosgene, trichloromethylformate or bistrichloromethylcarbonate, preferably phosgene or bistrichloromethylcarbonate, more preferably phosgene. An amount thereof may be mentioned, in general, a ratio of 1.0 to 1.5 equivalents in terms of phosgene per mole of the compound (II), preferably a ratio of 1.0 to 1.3 equivalents.

As the base (1) to be used, there may be mentioned an organic base or an inorganic base. As the organic base, there may be mentioned, for example, a tertiary amine such as triethylamine, tri-n-propylamine, tri-n-butylamine, diisopropylethylamine, N-methyl-piperidine or pyridine, etc., preferably triethylamine or tri-n-propylamine, more preferably triethylamine.

As the inorganic base, there may be mentioned, for example, an alkali metal carbonate such as sodium carbonate or potassium carbonate, an alkali metal hydrogen carbonate such as sodium hydrogen carbonate or potassium hydrogen carbonate, and an alkali metal hydroxide such as sodium hydroxide or potassium hydroxide, etc., preferably a carbonate or a hydrogen carbonate, more preferably sodium carbonate or potassium carbonate. As an amount of the base (1) to be used, there may be mentioned, in general, 1 to 2 equivalents per mole of the compound (II), preferably a ratio of 1.2 to 1.7 equivalents.

As the solvent to be used, it is not particularly limited so long as it does not directly participate in the present reaction, and may be mentioned an organic solvent alone or a combination of an organic solvent and water. As the organic solvent, there may be mentioned, for example, an aromatic hydrocarbon such as benzene, toluene, xylene, etc., a chlorinated hydrocarbon such as chlorobenzene, dichlorobenzene, methylene chloride, chloroform, carbon tetrachloride, 1,2-dichloroethane, etc., an ester such as methyl acetate, ethyl acetate, butyl acetate, etc., and an ether such as diisopropyl ether, dibutyl ether, dimethoxyethane, tetrahydrofuran, dioxane, etc., preferably an aromatic hydrocarbon or an ether, more preferably toluene.

A mixing ration of the organic solvent and water is optional. As an amount of the organic solvent or the combination of the organic solvent and water, there may be mentioned in general a range of each 0.1 to 6.0 liters per mole of N-substituted-α-amino acid ester, preferably in the range of 0.2 to 3.0 liters. It is possible to use a large amount of the solvent exceeding the upper limit thereof but there is no merit to do so. Also, when an organic base is used as a base, it is preferred to use the organic solvent alone, while an inorganic base is used, a mixed solvent of the organic solvent and water is preferred.

The reaction temperature may vary depending on the kinds of N-substituted-α-amino acid ester, the chlorocarbonylating agent, the base and the solvent, but generally in the range of 0 to 80° C., preferably 0 to 50° C.

The reaction time may vary depending on the reaction temperature, etc., but generally in the range of 0.5 to 10 hours, preferably in the range of 0.5 to 5 hours.

The reaction may be carried out in the presence of an inert gas such as nitrogen, argon, helium, etc.

After completion of the first step, the compound (III) may not necessary be isolated. In the case of using a mixed solvent of the organic solvent and water, an aqueous layer is separated by liquid-separating operation and the resulting organic solvent solution can be transferred to the next step. Moreover, depending on necessity, washing the solvent with water, dehydration of the organic solvent by a dryer, etc., may be incorporated. When an organic solvent alone is used, the formed hydrochloride, etc. of the base (1) is removed by a filtrating operation, etc., and washing the solvent with water, dehydration of the organic solvent by a dryer, etc., may be incorporated.

The second step is a step of preparing the compound (I), and is accomplished by subjecting intramolecular cyclization of the compound (III) in the presence of a base (2).

As the base (2) to be used, there may be mentioned, for example, a tertiary amine such as triethylamine, tri-n-propylamine, tri-n-butylamine, diisopropylethylamine, N-methyl-piperidine, pyridine, etc., an alkali metal carbonate such as sodium carbonate, potassium carbonate, etc., sodium hydride, sodium amide, lithium diisopropylamide, lithium bistrimethylsilylamide, etc., preferably a tertiary amine such as triethylamine. An amount of the base (2) to be used is generally in the range of 1.0 to 5.0-fold moles per mole of the N-substituted-a-amino acid ester, preferably in the range of 1.0 to 3.0-fold moles.

As the practicing method of the second step, a base (2) is added to an organic solvent mixture containing the compound (III) obtained in the first step to react them, or the reaction may be carried out by adding an organic solvent solution containing an organic base to an organic solvent solution containing the compound (III) obtained in the first step. In this case, an amount of the solvent to be used for dissolving the organic base is 0.1 to 0.5 liter based on 1 mole of N-substituted-α-amino acid esters. Moreover, the organic solvent mixture solution containing the compound (III) obtained in the first step is condensed and the compound (III) is isolated, and then an organic solvent and the base (2) may be added thereto to react these materials. The organic solvent to be used in this case is the same as the organic solvent and an amount thereof which can be used in the first step.

The reaction temperature may vary depending on the kind of the compound (III), the form of the compound (III) to be used, the base (2) and the organic solvent, etc., and generally in the range of −78 to 150° C., preferably room temperature to 120° C.

The reaction time can be optionally selected depending on the reaction temperature, and generally selected in the range of 1 to 12 hours.

The reaction may be carried out in the presence of an inert gas such as nitrogen, argon, helium, etc.

The method of obtaining a reaction mixture containing the formed compound (III) in the present invention may be carried out by combining the usual washing operation and separating operation. For example, the formed salt is removed by filtration operation, the filtrate is washed with water, followed by dehydration by a drier, and removal operation by condensation of an organic solvent, etc. to obtain a crude product of the compound (III). When the compound is further purified, purification may be carried out by the conventionally known means such as column chromatography, recrystallization, etc.

Also, the compound (I) of the present invention may be obtained by applying the specific preparation methods described in Examples.

From the thus obtained 5-alkoxy-2(3H)-oxazolone compound, 4-carboalkoxy-2-oxazolidinones represented by the formula (V) can be led according to the method of the above-mentioned reaction scheme (1). Specific examples are shown in Reference example 1 described below.

In the preparation method of the reaction scheme (2) as mentioned above, there may be preferably mentioned 1) a preparation process of the reaction scheme (2) in which $R^1$ is a hydrogen atom, a $C_1$ to $C_{10}$ alkyl group which may be substituted, a $C_3$ to $C_{10}$ cycloalkyl group which may be substituted, a $C_2$ to $C_{10}$ alkenyl group which may be substituted or a phenyl group which may be substituted, 2) a preparation process of the reaction scheme (2) in which $R^1$ is a $C_1$ to $C_{10}$ alkyl group which may be substituted, 3) a preparation process of the reaction scheme (2) in which $R^1$ is a benzyl group, a 4-methylbenzyl group, an a 1-phenylethyl group, a diphenylmethyl group, a 1-(1-naphthyl)ethyl group, a furfuryl group, an isopropyl group, a methyl group, a (1-naphthyl)methyl group, a 3,4-dimethoxybenzyl group or a phenyl group, 4) a preparation process of the reaction scheme (2) in which $R^2$ is a hydrogen atom, a $C_1$ to $C_{10}$ alkyl group which may be substituted, a phenyl group which may be substituted or an unsubstituted $C_2$ to $C_{10}$ alkenyl group, 5) a preparation process of the reaction scheme (2) in which $R^2$ is a hydrogen atom or a $C_1$ to $C_{10}$ alkyl group which may be substituted, 6) a preparation process of the reaction scheme (2) in which $R^2$ is a hydrogen atom, a methyl group, an ethyl group, a propyl group or an isopropyl group, 7) a preparation process of the reaction scheme (2) in which $R^3$ is a $C_1$ to $C_{10}$ alkyl group which may be substituted, a $C_3$ to $C_{10}$ cycloalkyl group which may be substituted, a $C_2$ to $C_{10}$ alkenyl group which may be substituted (provided that a 2-alkenyl group is excluded) or a phenyl group which may be substituted, 8) a preparation process of the reaction scheme (2) in which $R^3$ is a $C_1$ to $C_6$ alkyl group which may be substituted, a $C_3$ to $C_{10}$ alkenyl group which may be substituted (provided that a 2-alkenyl group is excluded), a $C_3$ to $C_6$cycloalkyl group which may be substituted or a phenyl group which may be substituted, 9) a preparation process of the reaction scheme (2) in which $R^3$ is a methyl group, an ethyl group, a propyl group, an isopropyl group, a 4-pentenyl group, a cyclohexyl group, a menthyl group, a 8-phenylmenthyl group or a phenyl group, 10) a preparation process of the reaction scheme (2) in which the chlorocarbonylating agent is phosgene, trichloromethylchloroformate or bistrichloromethylcarbonate, 11) a preparation process of the reaction scheme (2) in which the chlorocarbonylating agent is phosgene or bistrichloromethylcarbonate, 12) a preparation process of the reaction scheme (2) in which the chlorocarbonylating agent is phosgene, 13) a preparation process of the reaction scheme (2) in which an amount of the chlorocarbonylating agent to be used is 1.0 to 1.5 equivalents in terms of phosgene based on 1 mole of N-substituted-a-amino acid esters, 14) a preparation process of the reaction scheme (2) in which an amount of the chlorocarbonylating agent to be used is 1.0 to 1.3 equivalents in terms of phosgene based on 1 mole of N-substituted-α-amino acid esters, 15) a preparation process of the reaction scheme (2) in which the base (1) is an organic base or an inorganic base, 16) a preparation process of the reaction scheme (2) in which the base (1) is an organic base, 17) a preparation process of the reaction scheme (2) in which an organic base is a tertiary amine such as triethylamine, tri-n-propylamine, tri-n-butylamine, diisopropylethylamine, N-methyl-piperidine or pyridine, etc., 18) a preparation process of the reaction scheme (2) in which an organic base is triethylamine or tri-n-propylamine, 19) a preparation process of the reaction scheme (2) in which an organic base is triethylamine, 20) a preparation process of the reaction scheme (2) in which the base (1) is an inorganic base, 21) a preparation process of the reaction scheme (2) in which an inorganic base is an alkali metal carbonate such as sodium carbonate or potassium carbonate, an alkali metal hydrogen carbonate such as sodium hydrogen carbonate or potassium hydrogen carbonate, or an alkali metal hydroxide such as sodium hydroxide or potassium hydroxide, etc., 22) a preparation process of the reaction scheme (2) in which an inorganic base is an alkali metal carbonate or an alkali metal hydrogen carbonate, 23) a preparation process of the reaction scheme (2) in which an inorganic base is sodium carbonate or potassium carbonate, 24) a preparation process of the reaction scheme (2) in which an amount of the base (1) to be used is 1 to 2 equivalents based on one mole of N-substituted-a-amino acid esters, 25) a preparation process of the reaction scheme (2) in which an amount of the base (1) to be used is 1.2 to 1.7 equivalents based on one mole of N-substituted-a-amino acid esters, 26) a preparation process of the reaction scheme (2) in which the solvent is an organic solvent alone or an organic solvent and water, 27) a preparation process of the reaction scheme (2) in which the solvent is an organic solvent, 28) a preparation process of the reaction scheme (2) in which an organic solvent is an aromatic hydrocarbon such as benzene, toluene, xylene, etc., a chlorinated hydrocarbon such as chlorobenzene, dichlorobenzene, methylene chloride, chloroform, carbon tetrachloride, 1,2-dichloroethane, etc., an ester such as methyl acetate, ethyl acetate, butyl acetate, etc., and an ether such as diisopropyl ether, dibutyl ether, dimethoxyethane, tetrahydrofuran, dioxane, etc., 29) a preparation process of the reaction scheme (2) in which an organic solvent is an aromatic hydrocarbon or an ether, 30) a preparation process of the reaction scheme (2) in which an organic solvent is toluene, 31) a preparation process of the reaction scheme (2) in which an amount of an organic solvent or an organic solvent and water to be used is 0.1 to 6.0 liters based on one mole of N-substituted-a-amino acid esters, 32) a preparation process of the reaction scheme (2) in which an amount of an organic solvent or an organic solvent and water to be used is 0.2 to 3.0 liters based on one mole of N-substituted-a-amino acid esters, 33) a preparation process of the reaction scheme (2) in which the base (2) is a tertiary amine such as triethylamine, tri-n-propylamine, tri-n-butylamine, diisopropylethylamine, N-methyl-piperidine, pyridine, etc., an alkali metal carbonate such as sodium carbonate, potassium carbonate, etc., sodium hydride, sodium amide, lithium diisopropylamide, lithium bistrimethylsilylamide, etc., and 34) a preparation process of the reaction scheme (2) in which the base (2) is a tertiary amine such as triethylamine, etc.

Moreover, it is more preferred 35) a preparation process of the reaction scheme (2) in which an amount of the base (2) to be used is in the range of 1.0 to 5.0-fold moles based on one mole of N-substituted-α-amino acid esters, 36) a preparation process of the reaction scheme (2) in which an amount of the base (2) to be used is in the range of 1.0 to 3.0-fold moles based on one mole of N-substituted-α-amino acid esters, also, a preparation process of the reaction scheme (2) obtained by selecting $R^1$ from 1) to 3), selecting $R^2$ from 4) to 6), selecting $R^3$ from 7) to 9), selecting the chlorocarbonylating agent from 10) to 12), selecting an amount of the chlorocarbonylating agent from 13) to 14), selecting the base (1) from 15) to 23), selecting an amount of the base (1) from 24) to 25), selecting the solvent from 26) to 30), selecting an amount of the solvent from 31) to 32), selecting the base (2) from 33) to 34) and selecting an amount of the base (2) from 35) to 36), and optionally combining these is preferred.

Utilizability in industry

According to the present invention, 5-alkoxy-2(3H)-oxazolone compounds can be obtained by reacting N-substituted-α-amino acid esters and a chlorocarbonylating agent in the presence of a base in a solvent, and the resulting reaction mixture containing a compound (II) is subjected to intramolecular cyclization reaction in the presence of a base. The resulting 5-alkoxy-2 (3H)-oxazolone compounds are useful as a starting material of β-hydroxy-α-amino acids which are used as a drug substance, an intermediate or a starting material.

EXAMPLES

In the following, the present invention will be explained in more detail by referring to Examples, but the scope of the present invention is not limited by these.

EXAMPLE 1

Synthesis of 3-benzyl-5-(l)-menthyloxy-2(3H)-oxazolone

In 15 ml of toluene was dissolved 3.03 g (10 mmol) of N-benzyl-glycine-(l)-menthyl ester to obtain a toluene solution. To the resulting toluene solution was added an aqueous solution in which 0.58 g of anhydrous sodium carbonate had been dissolved in 15 ml of water, and cooling the mixture to 0° C. while stirring, 1.09 g (11 mmol) of a phosgene gas was blown to react these materials. After completion of the phosgene blowing, the mixture was further stirred at 0 to 5° C. for one hour.

After completion of the reaction, the aqueous layer was separated from the resulting reaction mixture (1). The toluene layer was dried over anhydrous magnesium sulfate and filtered, and then, 2.02 g (20mmol) of triethylamine was added to the filtrate and the mixture was allowed to react at 100 to 105° C. for 8 hours.

After completion of the reaction, the resulting reaction mixture (2) was cooled to room temperature and precipitated triethylamine hydrochloride was separated by filtration. The filtrate was concentrated under reduced pressure, 30 ml of methanol was added to the residue and the mixture was cooled at 0 to 5° C. Precipitated crystals were collected by filtration, and the resulting crystals were dried at 30° C. under reduced pressure to obtain 2.5 g (7.6 mmol) of 3-benzyl-5-(l)-menthyloxy-2(3H)-oxazolone as pale yellow crystals. (Yield based on N-benzyl-glycine-(l)-menthyl ester=76%)

Melting point: 88 to 93° C.

IR (KBr, cm$^{-1}$): 1678, 1693, 1760

$^1$H-NMR (δ, CDCl$_3$): 0.80 (d, J=6.8Hz, 3H), 0.7–2.2 (m, 15H), 3.86 (td, J=4.4Hz, J=10.7Hz), 4.63 (d, J=15.1 Hz. 1H), 4.69 (d, J=15.1Hz, 1H), 5.53 (s, 1H), 7.26–7.39 (m, 5H)

MS (CI, i-C$_4$H$_{10}$) m/z 330 (MH$^+$)

EXAMPLE 2

Synthesis of 3-(4-methylbenzyl)-4-methyl-5-methoxy-2(3H)-oxazolone

In 20 ml of toluene was dissolved 2.89 g (14 mmol) of methyl 2-(N-(4-methylbenzyl)amino)propionate to obtain a toluene solution. To the resulting toluene solution was added an aqueous solution in which 0.84 g of anhydrous sodium carbonate had been dissolved in 30 ml of water. The mixture was stirred at room temperature and 1.63 g (16.5 mmol) of a phosgene gas was blown therein to react these materials.

After completion of the blowing, the mixture was further stirred at room temperature for one hour.

After completion of the reaction, the aqueous layer was separated from the resulting reaction mixture (1). The toluene layer was dried over anhydrous magnesium sulfate and filtered, and then, 3.03 g (30 mmol) of triethylamine was added to the filtrate and the mixture was allowed to react at 120° C. for 2 hours.

After completion of the reaction, the resulting reaction mixture (2) was cooled to room temperature and precipitated triethylamine hydrochloride was separated by filtration. The filtrate was concentrated under reduced pressure to obtain 2.81 g (12 mmol) of 3-(4-methylbenzyl)-4-methyl-5-methoxy-2 (3H)-oxazolone as pale yellow viscous liquid. (Yield based on methyl 2-(N-(4-methylbenzyl)amino) propionate=86%)

$^1$H-NMR (δ, CDCl$_3$): 1.82 (s, 3H), 2.34 (s, 3H), 3.80 (s, 3H), 4.68 (s, 2H), 7.12 (s, 4H)

MS (EI) m/z 233 (M$^+$)

EXAMPLE 3

Synthesis of 3-(1-phenylethyl)-5-methoxy-2(3H)-oxazolone

In 30 ml of toluene was dissolved 5.79 g (30 mmol) of N-(1-phenylethyl)-glycine methyl ester to obtain a toluene solution. To the resulting toluene solution was added an aqueous solution in which 1.75 g of anhydrous sodium carbonate had been dissolved in 30 ml of water. The mixture was stirred at room temperature and 3.26 g (33 mmol) of a phosgene gas was blown to react these materials. After completion of the phosgene blowing, the mixture was further stirred at room temperature for one hour.

After completion of the reaction, the aqueous layer was separated from the resulting reaction mixture (1). The toluene layer was dried over anhydrous magnesium sulfate and filtered, and then, 6.06 g (60mmol) of triethylamine was added to the filtrate and the mixture was allowed to react at 120° C. for 3 hours.

After completion of the reaction, the reaction mixture was cooled to room temperature and precipitated triethylamine hydrochloride was separated by filtration. The filtrate was concentrated under reduced pressure, then, 20 ml of toluene and 100 ml of n-hexane were added to the resulting residue to effect recrystallization to obtain 5.02 g (22.9 mmol) of 3-(1-phenylethyl)-5-methoxy-2(3H)-oxazolone as white crystals. (Yield based on N-(1-phenylethyl)-glycine methyl ester=76%)

Melting point: 68 to 71° C.

IR (KBr, cm$^{-1}$): 1682, 1750

$^1$H-NMR (δ, CDCl$_3$): 1.66 (d, J=7.3Hz, 3H), 3.75 (s, 3H), 5.32 (q, J=7.3Hz, 1H), 5.43 (s, 1H), 7.2–7.4 (m, 5H)

MS (EI) m/z 219 (M$^+$)

Elemental analysis; Calcd: C, 65.74; H, 5.98; N, 6.39. Found: C, 65.47, H. 5.99; N, 6.35.

EXAMPLE 4

Synthesis of 3-((s)-1-phenylethyl)-5-isopropoxy-2 (3H)-oxazolone

In 300 ml-volume flask were charged 3.71 g (37.5 mmol) of bistrichloromethylcarbonate and 100 ml of toluene, and after cooling to 0° C., a mixed solution of 5.53 g (25.0 mmol) of N-((s)-1-phenylethyl)-glycine isopropyl ester, 3.79 g (37.5 mmol) of triethylamine and 60 ml of toluene was added dropwise to the above mixture over 0.5 hour, and stirring was further carried out for one hour to effect the reaction.

After completion of the reaction, 100 ml of a saturated aqueous sodium chloride solution was added to the resulting reaction mixture (1), and the layers were separated. The resulting organic layer was dried over anhydrous magnesium sulfate followed by filtration. To the filtrate was added 5.05 g (50.0 mmol) of triethylamine and stirring was carried out at 120° C. for 4 hours to effect the reaction.

After completion of the reaction, insolubles were removed by filtration from the resulting reaction mixture (2), and 100 ml of a saturated aqueous ammonium chloride solution was added to the filtrate. The liquids were separated and the organic layer was washed with 100 ml of a saturated aqueous sodium chloride solution. The resulting organic layer was dried over anhydrous magnesium sulfate followed by filtration, and the filtrate was concentrated to obtain 6.04 g (24.4 mmol) of 3- ((s)-1-phenylethyl)-5-isopropoxy-2 (3H)-oxazolone as a brownish oily substance. (Yield based on N-((s)-1-phenylethyl)-glycine isopropyl ester=98%)

IR (neat, cm$^1$): 1682, 1750

$^1$H-NMR (δ, CDCl$_3$): 1.27 (d, J=6.4Hz, 6H), 1.66 (d, J=6.8Hz, 3H), 4.30 (m, 1H), 5.25 (q, J=6.8Hz, 1H), 5.58 (s, 1H), 7.22–7.37 (m, 5H)

MS (CI, i-C$_4$H$_{10}$) m/z 248 (MH$^+$)

EXAMPLE 5

Synthesis of 3-((R)-1-phenylethyl)-5-methoxy-2 (3H)-oxazolone

In 15 ml of toluene was dissolved 2.89 g (15 mmol) of N-((R)-1-phenylethyl)-glycine methyl ester to obtain a toluene solution. To the resulting toluene solution was added an aqueous solution in which 0.88 g of anhydrous sodium carbonate had been dissolved in 15 ml of water. The mixture was stirred at room temperature and 1.63 g (16.5 mmol) of a phosgene gas was blown to react these materials. After completion of the blowing, the mixture was further stirred at room temperature for one hour.

After completion of the reaction, the aqueous layer was separated from the resulting reaction mixture (1). The toluene layer was dried over anhydrous magnesium sulfate and filtered, and then, 3.03 g (30 mmol) of triethylamine was added to the filtrate and the mixture was allowed to react at 120° C. for 3 hours. After completion of the reaction, the reaction mixture was cooled to room temperature and precipitated triethylamine hydrochloride was separated by filtration. The filtrate was concentrated under reduced pressure, then, 10 ml of toluene and 50 ml of n-hexane were added to the resulting residue to effect recrystallization to obtain 2.2 g (10 mmol) of 3- ((R)-1-phenylethyl) -5-methoxy-2 (3H)-oxazolone as white crystals. (Yield based on N-((R)-1-phenylethyl)-glycine methyl ester=67%)

Melting point: 49 to 52° C.

IR (KBr, cm$^{-1}$): 1682, 1750

$^1$H-NMR (δ, CDCl$_3$): 1.66 (d, J=7.3Hz, 3H), 3.75 (s, 3H), 5.32 (q, J=7.3Hz, 1H), 5.43 (s, 1H), 7.2–7.42 (m, 5H)

MS (CI, i-C$_4$H$_{10}$) m/z 220 (MH$^+$)

Elemental analysis; Calcd: C, 65.74; H, 5.98; N, 6.39. Found: C, 65.78, H, 6.08; N, 6.48.

EXAMPLE 6

Synthesis of 3-diphenylmethyl-5-methoxy-2(3H)-oxazolone

In 15 ml of toluene was dissolved 1.79 g (7 mmol) of N-diphenylmethyl-glycine methyl ester to obtain a toluene solution. To the resulting toluene solution was added an aqueous solution in which 0.41 g of anhydrous sodium carbonate had been dissolved in 15 ml of water. The mixture was stirred at room temperature and 0.76 g (7.7 mmol) of a phosgene gas was blown to react these materials. After completion of the blowing, the mixture was further stirred at room temperature for one hour.

After completion of the reaction, the aqueous layer was separated from the resulting reaction mixture (1). The toluene layer was dried over anhydrous magnesium sulfate and filtered, and then, 1.41 g (14 mmol) of triethylamine was added to the filtrate and the mixture was allowed to react for 10 hours under reflux by heating.

After completion of the reaction, the reaction mixture (2) was cooled to room temperature and precipitated triethylamine hydrochloride was separated by filtration. The filtrate was washed with a saturated aqueous sodium chloride solution, and the toluene layer was dried over anhydrous magnesium sulfate followed by filtration. The filtrate was concentrated under reduced pressure, then, 10 ml of toluene and 50 ml of n-hexane were added to the resulting residue to effect recrystallization to obtain 1.3 g (4.6 mmol) of 3-diphenylmethyl-5-methoxy-2 (3H)-oxazolone as white crystals. (Yield based on N-diphenylmethyl-glycine methyl ester=66%)

Melting point: 125 to 127° C.
IR (KBr, cm$^{-1}$): 1682, 1756
$^1$H-NMR (δ, CDCl$_3$): 3.73 (s, 3H)$_1$ 5.40 (s, 1H), 6.47 (s, 1H), 7.1–7.5 (m, 10H)
MS (CI, i-C$_4$H$_{10}$) m/z 282 (MH$^+$)
Elemental analysis; Calcd: C, 72.58; H, 5.37; N, 4.98. Found: C, 72.45, H, 5.40; N, 4.98.

EXAMPLE 7

Synthesis of 3-diphenylmethyl-4-methyl-5-methoxy-2(3H)-oxazolone

In a 300 ml-volume three-necked flask were charged 2.97 g (30.0 mmol) of bistrichloromethylcarbonate and 60 ml of toluene, and after cooling to 0° C., a mixed solution of 4.04 g (15.0 mmol) of N-diphenylmethyl-alanine methyl ester, 3.03 g (30.0 mmol) of triethylamine and 60 ml of toluene was added dropwise to the above mixture over one hour. Thereafter, the temperature of the mixture was raised to 100° C. with a temperature raising ratio of 10° C./hour and stirring was carried out for further two hours to effect the reaction.

After completion of the reaction, insolubles were removed by filtration from the resulting reaction mixture (1), and 100 ml of a saturated aqueous ammonium chloride solution was added to the filtrate. The liquids were separated and the organic layer was washed with 100 ml of a saturated aqueous sodium chloride solution. The resulting organic layer was dried over anhydrous magnesium sulfate followed by filtration, and the filtrate was concentrated to obtain 4.21 g (14.3 mmol) of 3-diphenylmethyl-4-methyl-5-methoxy-2 (3H)-oxazolone as a brownish oily substance. (Yield based on N-diphenylmethyl-alanine methyl ester=95%)

IR (neat, cm$^{-1}$): 1718, 1775
$^1$H-NMR (δ, CDCl$_3$): 1.53 (s, 3H), 3.81 (s, 3H), 6.59 (s, 1H), 7.23–7.38 (m, 10H)
MS (CI, i-C$_4$H$_{10}$) m/z 296 (MH$^+$)

EXAMPLE 8

Synthesis of 3-diphenylmethyl-5-(l)-menthyloxy-2 (3H)-oxazolone

In 15 ml of toluene was dissolved 3.8 g (10 mmol) of N-diphenylmethyl-glycine-(l)-menthyl ester to obtain a toluene solution. To the resulting toluene solution was added an aqueous solution in which 0.58 g of anhydrous sodium carbonate had been dissolved in 15 ml of water. While stirring at room temperature, 1.09 g (11 mmol) of a phosgene gas was blown to react these materials. After completion of the blowing, the mixture was further stirred at room temperature for one hour.

After completion of the reaction, the aqueous layer was separated from the resulting reaction mixture (1). The toluene layer was dried over anhydrous magnesium sulfate and filtered, and then, 2.02 g (20 mmol) of triethylamine was added to the filtrate and the mixture was refluxed under heating for 5 hours. After completion of the reaction, the reaction mixture was cooled to room temperature and precipitated triethylamine hydrochloride was separated by filtration. The filtrate was concentrated under reduced pressure, 20 ml of methanol was added to the residue and the mixture was allowed to stand at room temperature. Precipitated crystals were collected by filtration, and the resulting crystals were dried at 25° C. under reduced pressure to obtain 2.5 g (6.2 mmol) of 3-diphenylmethyl-5- (1)-menthyloxy-2 (3H)-oxazolone as white crystals. (Yield based on N-diphenylmethyl-glycine-(1)-menthyl ester=62%)

Melting point: 121 to 123° C.
IR (KBr, cm$^{-1}$) : 1670, 1749
$^1$H-NMR (δ, CDCl$_3$): 0.79 (d, J=7.3Hz, 3H), 0.8–0.9 (m, 1H), 0.90 (d, J=7.3Hz, 3H), 0.91 (d, J=6.5Hz, 3H), 0.95–1.10 (m, 2H), 1.3–1.5 (m, 2H), 1.6–1.7 (m, 2H), 2.0–2.1 (m, 1H), 2.1–2.2 (m, 1H), 3.88 (td, J=4.4Hz and J=10.8Hz, 1H), 5.51 (S, 1H), 6.47 (s, 1H), 7.1–7.2 (m, 5H), 7.3–7.4 (m, 5H)
MS (CI, i-C$_4$H$_{10}$) m/z 406 (MH$^+$)
Elemental analysis; Calcd: C, 77.01; H, 7.70; N, 3.45. Found: C, 77.10; H, 7.82; N, 3.47.

EXAMPLE 9

Synthesis of 3-diphenylmethyl-5-((1S,2S,5R)-5-methyl-2-(1-methyl-1-phenylethyl)cyclohexyloxy)-2 (3H)-oxazolone In 10 ml of toluene was dissolved 1.0 g (2.1 mmol) of N-diphenylmethyl-glycine-((1S,2S,5R)-5-methyl-2-(1-methyl-1-phenylethyl) cyclohexyl) ester to obtain a toluene solution. To the resulting toluene solution was added an aqueous solution in which 0.12 g of anhydrous sodium carbonate had been dissolved in 10 ml of water. While stirring at room temperature, 0.23 g (2.3 mmol) of a phosgene gas was blown to react these materials. After completion of the blowing, the mixture was further stirred at room temperature for one hour.

After completion of the reaction, the aqueous layer was separated from the resulting reaction mixture (1). The toluene layer was dried over anhydrous magnesium sulfate and filtered, and then, 0.4 g (4 mmol) of triethylamine was added to the filtrate and the mixture was refluxed under heating for 3 hours.

After completion of the reaction, the resulting reaction mixture (2) was cooled to room temperature and precipitated triethylamine hydrochloride was separated by filtration. The filtrate was washed with a saturated aqueous sodium chloride solution, and the toluene layer was dried over anhydrous magnesium sulfate followed by filtration. The filtrate was concentrated under reduced pressure, and the residue was applied to silica gel column chromatography (eluent; n-hexane:ethyl acetate=9:1 (volume ratio)) to obtain 0.95 g (2 mmol) of 3-diphenylmethyl-5-((1S,2S,5R)-5-methyl-2-(1-methyl-1-phenylethyl)cyclohexyloxy)-2(3H)-oxazolone as white crystals. (Yield based on N-diphenylmethyl-glycine-((1S,2S,5R)-5-methyl-2-(1-methyl-1-phenylethyl)cyclohexyl) ester=95%)

Melting point: 118 to 120° C.

IR (KBr, cm$^{-1}$): 1687, 1775

$^1$H-NMR (δ, CDCl$_3$): 0.86 (d, J=6.35 Hz, 3H), 1.34 (s, 3H), 1.39 (s, 3H), 0.7–2.1 (m, 8H), 3.95 (td, J=4.4 Hz, J=10.74 Hz, 1H), 5.31 (s, 1H), 6.45 (s, 1H), 7.09–7.40 (m, 15H)

MS (CI, i-C$_4$H$_{10}$) m/z 482 (MH$^+$)

EXAMPLE 10

Synthesis of 3-((R)-1-(1-naphthyl)ethyl)-5-methoxy-2(3H)-oxazolone

In 15 ml of toluene was dissolved 3.0 g (12.3 mmol) of N-((R)-1-(1-naphthyl) ethyl)-glycine methyl ester to obtain a toluene solution. To the resulting toluene solution was added an aqueous solution in which 0.72 g of anhydrous sodium carbonate had been dissolved in 15 ml of water. While stirring at room temperature, 1.34 g (13.5 mmol) of a phosgene gas was blown to react these materials. After completion of the blowing, the mixture was further stirred at room temperature for 2 hours.

After completion of the reaction, the aqueous layer was separated from the resulting reaction mixture (1). The toluene layer was dried over anhydrous magnesium sulfate and filtered, and then, 2.48 g (24.6 mmol) of triethylamine was added to the filtrate and the mixture was heated to 120° C. for 6 hours. After completion of the reaction, the reaction mixture was cooled to room temperature and precipitated triethylamine hydrochloride was separated by filtration. The filtrate was washed with a saturated aqueous sodium chloride solution, and the toluene layer was dried over anhydrous magnesium sulfate followed by filtration. The filtrate was concentrated under reduced pressure, and the residue was purified by applying it to silica gel column chromatography (eluent; n-hexane:ethyl acetate=5:1 (volume ratio)) to obtain 2.0 g (7.43 mmol) of 3-((R)-1-(1-naphthyl)ethyl)-5-methoxy-2(3H)-oxazolone as white crystals. (Yield based on N-((R)-1-(1-naphthyl)ethyl)-glycine methyl ester=60%)

Melting point: 89 to 91° C.

IR (KBr, cm$^{-1}$): 1676, 1762

$^1$H-NMR (δ, CDCl$_3$): 1.81 (d, J=6.6Hz), 3.62 (s, 3H), 5.19 (s, 1H), 6.05 (q, J=6.6Hz, 1H), 7.4–7.69 (m, 4H), 7.8–7.9 (m, 2H), 8.10 (d, J=8.8Hz, 1H)

MS (CI, i-C$_4$H$_{10}$) m/z 270 (MH$^+$)

Elemental analysis; Calcd: C, 71.36; H, 5.61; N, 5.21. Found: C, 71.26; H, 5.68; N, 5.12.

EXAMPLE 11

Synthesis of 3-furfuryl-4-ethyl-5-methoxy-2 (3H)-oxazolone

A mixed solution was obtained by adding 19.7 g (0.1 mmol) of 4-methyl 2-(N-furfurylamino)butyrate, 50 ml of toluene, 7.95 g of sodium carbonate and 75 ml of water. The resulting mixed solution was stirred at room temperature and 11.9 g of phosgene was blown thereinto at 35° C. or lower to effect the reaction (one hour). After completion of the blowing, the mixture was further stirred at room temperature for 30 minutes.

After completion of the reaction, the toluene layer was obtained by liquid separation from the resulting reaction mixture (1). The toluene layer was dried over anhydrous magnesium sulfate, and 15.18 g (0.15 mmol) of triethylamine was added to the resulting toluene solution and the mixture was reacted at 100° C. for 8 hours.

After completion of the reaction, the resulting reaction mixture (2) was cooled to room temperature and precipitated triethylamine hydrochloride was separated by filtration. The filtrate was washed with 0.5N hydrochloric acid and a saturated aqueous sodium chloride solution, and the toluene layer was dried over anhydrous magnesium sulfate followed by filtration. The filtrate was concentrated under reduced pressure, and the residue was purified by applying to silica gel column chromatography (eluent; n-hexane:ethyl acetate=5 : 1 (volume ratio)) to obtain 11.0 g (49.3 mmol) of 3-furfuryl-4-ethyl-5-methoxy-2(3H)-oxazolone as yellowish oily liquid. (Yield based on 4-methyl 2-(N-furfurylamino)butyrate=49%)

IR (KBr, cm$^{-1}$): 1725, 1785

$^1$H-NMR (δ, CDCl$_3$): 1.13 (t, 3H), 2.37 (q, 2H), 3.78 (s, 3H), 4.69 (s, 2H), 6.3–6.38 (m, 2H), 7.33–7.38 (m, 1H)

$^{13}$C-NMR (ppm, CDCl$_3$): 12.3, 14.9, 38.2, 61.2, 106.8, 108.4, 110.5, 142.3, 144.1, 149.1, 151.3

MS (CI, i-C$_4$H$_{10}$) m/z 224 (MH$^+$)

EXAMPLE 12

Synthesis of 3-furfuryl-4-ethyl-5-(4-pentenyl)oxy-2 (3H)oxazolone

By adding 25.1 g (0.1 mmol) of 4-pentenyl 2-(N-furfurylamino)butyrate, 50 ml of toluene, 8.0 g of sodium carbonate and 80 ml of water, and the mixture was stirred at room temperature. Into the resulting mixture was blown at 11.9 g of phosgene at 35° C. or lower (one hour), and after completion of the blowing, the mixture was further stirred at room temperature for 30 minutes. Then, the toluene layer was obtained by liquid separation. The toluene layer was dried over anhydrous magnesium sulfate, and 15.18 g (0.15 mmol) of triethylamine was added to the resulting toluene solution and the mixture was reacted at 100° C. for 8 hours.

After completion of the reaction, the resulting reaction mixture (1) was cooled to room temperature and precipitated triethylamine hydrochloride was separated by filtration. The filtrate was washed with 0.5N hydrochloric acid and a saturated aqueous sodium chloride solution, and the toluene layer was dried over anhydrous magnesium sulfate followed by filtration. The filtrate was concentrated under reduced pressure. Among the residue obtained, 5 g thereof was purified by applying to silica gel column chromatography (eluent; n-hexane:ethyl acetate=5:1 (volume ratio)) to obtain 2.2 g (7.94 mmol) of 3-furfuryl-4-ethyl-5-(4-pentenyl)oxy-2-(3H)oxazolone as yellowish oily liquid.

IR (KBr, cm$^{-1}$): 1718, 1775

$^1$H-NMR (δ, CDCl$_3$): 1.1 (t, 3H), 1.80 (qq, 2H), 2.19 (qd, 2H), 2.36 (q, 2H), 4.00 (t, 2H), 4.68 (s, 2H), 4.95–5.12 (m, 2H), 5.7–5.9 (m, 1H), 6.40 (d and dd, 2H), 7.35 (d, 1H)

MS (CI, i-C$_4$H$_{10}$) m/z 278 (MH$^+$)

EXAMPLE 13

Synthesis of 3-isopropyl-5-methoxy-2(3H)-oxazolone

In a 100 ml-volume three-necked flask were charged 809 mg (8.17 mmol) of bistrichloromethylcarbonate and 20 ml of toluene, and after cooling the mixture to 0° C., a mixed solution of 715 mg (5.45 mmol) of N-isopropyl-glycine methyl ester, 827 mg (8.17 mmol) of triethylamine and 20 ml of toluene was added dropwise to the above mixture over one hour. Thereafter, stirring was carried out for further two hours to effect the reaction.

After completion of the reaction, 40 ml of a saturated aqueous sodium chloride solution was added to the resulting reaction mixture (1). The liquids were separated and the organic layer was dried over anhydrous magnesium sulfate followed by filtration, and 1.65 g (16.3 mmol) of triethylamine was added to the filtrate and the mixture was reacted under stirring at 120° C. for 8 hours.

After completion of the reaction, 40 ml of a saturated aqueous ammonium chloride solution was added to the resulting reaction mixture (2). The liquids were separated and the organic layer was washed with 40 ml of a saturated aqueous sodium chloride solution. The organic layer was dried over anhydrous magnesium sulfate followed by filtration, and the filtrate was concentrated to obtain 699 mg (4.45 mmol) of 3-isopropyl-5-methoxy-2(3H)-oxazolone as a pale brownish crystal. (Yield based on N-isopropyl-glycine methyl ester=82%)

Melting point: 108 to 110° C.

IR (KBr, cm$^{-1}$): 1683, 1757

$^1$H-NMR ($\delta$, CDCl$_3$): 0.34 (d, J=6.3Hz, 6H), 2.84 (s, 3H), 3.30 (m, 1H), 4.64 (s, 1H)

MS (EI) m/z 157 (M$^+$)

$^{13}$C-NMR (ppm, CDCl$_3$) : 21.1, 45.4, 58.3, 84.4, 149.6, 150.2

EXAMPLE 14

Synthesis of 3-benzyl-5-methoxy-2(3H)-oxazolone

In 15 ml of toluene was dissolved 2.69 g (15 mmol) of N-benzyl-glycine methyl ester to obtain a toluene solution. To the resulting toluene solution was added an aqueous solution in which 0.88 g of anhydrous sodium carbonate had been dissolved in 20 ml of water. While stirring at room temperature, 1.63 g (16.5 mmol) of a phosgene gas was blown to react these materials. After completion of blowing the phosgene gas, the mixture was further stirred at room temperature for one hour.

After completion of the reaction, the aqueous layer was separated from the resulting reaction mixture (1). The obtained toluene layer was dried over anhydrous magnesium sulfate and filtered, and then, 3.03 g (30 mmol) of triethylamine was added to the filtrate and the mixture was heated to 120° C. for 15 hours.

After completion of the reaction, the resulting reaction mixture (2) was cooled to room temperature and precipitated triethylamine was separated by filtration. The filtrate was concentrated under reduced pressure, and the residue was purified by applying it to silica gel column chromatography (eluent; toluene:ethyl acetate=8:1 (volume ratio)) to obtain 0.8 g (3.9mmol) of 3-benzyl-5-methoxy-2 (3H)-oxazolone as white crystals. (Yield based on N-benzyl-glycine methyl ester=26%)

IR (KBr, cm$^{-1}$): 1681, 1770

$^1$H-NMR ($\delta$, CDCl$_3$): 3.73 (s, 3H), 4.68 (s, 2H), 5.42 (s, 1H), 7.18–7.50 (m, 5H)

MS (EI) m/z 205 (M$^+$)

EXAMPLE 15

Synthesis of 3-isopropyl-4-methyl-5-methoxy-2(3H)-oxazolone

In the same manner as in Example 14 except for using 1.45 g (10 mmol) of N-isopropyl-alanine methyl ester in place of N-benzyl-glycine methyl ester, 1.3 g (7.6 mmol) of 3-isopropyl-4-methyl-5-methoxy-2(3H)-oxazolone as a yellowish oily liquid. (Yield based on N-isopropyl-alanine methyl ester=76%)

$^1$H-NMR ($\delta$, CDCl$_3$): 1.43 (d, J=8.3Hz, 6H), 1.98 (s, 3H), 3.80 (s, 3H), 4.05 (q, J=8.3Hz, 1H)

$^{13}$C-NMR (ppm, CDCl$_3$) :7.1, 20.4, 45.8, 61.0, 100.8, 144.0, 150.5

MS (EI) m/z 171 (M$^+$)

EXAMPLE 16

Synthesis of 3-isopropyl-4-methyl-5-ethoxy-2(3H)-oxazolone

In the same manner as in Example 14 except for using 1.6 g (10 mmol) of N-isopropyl-alanine ethyl ester in place of N-benzyl-glycine methyl ester, 1.4 g (7.5 mmol) of 3-isopropyl-4-methyl-5-ethoxy-2(3H)-oxazolone as a yellowish oily liquid. (Yield based on N-benzyl-glycine ethyl ester=75%)

$^1$H-NMR ($\delta$, CDCl$_3$): 1.32 (d, J=6.3Hz, 3H), 1.43 (d, J=8.3Hz, 6H), 1.98 (s, 3H), 4.0–4.1 (m, 3H)

$^{13}$C-NMR (ppm, CDCl$_3$): 7.2, 14.7, 20.5, 45.9, 70.0, 101.8, 142.9, 150.8

MS (EI) m/z 185 (M$^+$)

IR (neat, cm$^{-1}$): 1770, 1710

EXAMPLE 17

Synthesis of 3-isopropyl-4-methyl-5-cyclohexyloxy-2(3H)-oxazolone

In the same manner as in Example 14 except for using 2.1 g (10 mmol) of N-isopropyl-alanine ester in place of N-benzyl-glycine methyl ester, 1.6 g (6.7 mmol) of 3-isopropyl-4-methyl-5-cyclohexyloxy-2(3H)-oxazolone as a yellowish oily liquid. (Yield based on N-isopropyl-alanine cyclohexyl ester =67%)

$^1$H-NMR ($\delta$, CDCl$_3$): 1.2–2.0 (m, 11H), 1.43 (d, J=8.0 Hz, 6H), 1.98 (s, 3H), 3.95–4.1 (m, 2H)

$^{13}$C-NMR (ppm, CDCl$_3$): 7.6, 20.6, 23.6, 25.3, 31.9, 46.0, 82.2, 102.6, 142.2, 151.0

MS (EI) m/z 239 (M$^+$)

EXAMPLE 18

Synthesis of 3-((R)-1-(1-naphthyl)ethyl)-5-isopropoxy-2(3H)-oxazolone

In the same manner as in Example 14 except for using 4.07 g (15 mmol) of N-( (R)-1-(1-naphthyl)ethyl)-glycine isopropyl ester in place of N-benzyl-glycine methyl ester, 2.9 g (9.75 mmol) of 3-((R)-1-(1-naphthyl)ethyl)-5-isopropoxy-2(3H)-oxazolone as a yellowish oily liquid. (Yield based on N-((R)-1-(1-naphthyl)ethyl)-glycine isopropyl ester=65%)

$^1$H-NMR ($\delta$, CDCl$_3$): 1.19 (t, J=6.4Hz, 6H), 1.80 (d, J=6.8Hz, 3H), 4.21 (m, 1H), 5.31 (s, 1H), 6.04 (q, J=6.8Hz, 1H), 7.4–7.6 (m, 4H), 7.8–7.9 (m, 2H), 8.09 (d, J=8.8Hz, 1H)

IR (neat, cm$^{-1}$): 1761, 1683

MS (EI) m/z 297 (M$^+$)

EXAMPLE 19

Synthesis of 3-((R)-1-phenylethyl)-4-methyl-5-methoxy-2(3H)-oxazolone

In a 100 ml-volume three-necked flask were charged 2.99 g (30 mmol) of bistrichloromethylcarbonate and 20 ml of toluene, and after cooling the mixture to 0° C., a mixed solution of 3.11 g (15 mmol) of N-((R)-1-phenylethyl)-alanine methyl ester, 3.03 g (30 mmol) of triethylamine and 20 ml of toluene was added dropwise to the above mixture over one hour. Thereafter, stirring was carried out for further two hours to effect the reaction.

After completion of the reaction, 40 ml of a saturated aqueous sodium chloride solution was added to the resulting reaction mixture (1). The liquids were separated and the organic layer was dried over anhydrous magnesium sulfate followed by filtration. To the filtrate was added 3.03 g (30 mmol) of triethylamine and the mixture was reacted under stirring at 120° C. for 8 hours.

After completion of the reaction, 40 ml of a saturated aqueous ammonium chloride solution was added to the resulting reaction mixture (2). The liquids were separated and the organic layer was washed with 40 ml of a saturated aqueous sodium chloride solution. The organic layer was dried over anhydrous magnesium sulfate followed by filtration, and the filtrate was concentrated to obtain a concentrated residue. The resulting concentrated residue was isolated and purified by silica gel column chromatography (eluent; n-hexane : ethyl acetate=6:1 (volume ratio)) to obtain 2.17 g (9.3 mmol) of 3-((R)-1-phenylethyl)-4-methyl-5-methoxy-2(3H)-oxazolone as a colorless transparent liquid (Yield based on N-((R)-1-phenylethyl)-alanine methyl ester=62%) and 1.62 g (7.0 mmol) of 3-((R)-1-phenylethyl)-4-methylene-5-methoxy-2-oxazolidinone as a colorless transparent liquid (Yield based on N-((R)-1-phenylethyl)-alanine methyl ester=36%)(a mixture of diastereomer 1:1).

3-((R)-1-phenylethyl)-4-methyl-5-methoxy-2(3H)-oxazolone $^1$H-NMR (δ, CDCl$_3$): 1.67 (s, 3H), 1.81 (d, J=7.3 Hz, 3H), 3.78 (s, 3H), 5.31 (q, J=7.3Hz, 1H), 7.28–7.37 (m, 5H)

IR (KBr, cm$^{-1}$): 1774, 1718

MS (EI) m/z 233 (M$^+$)

3-((R)-1-phenylethyl)-4-methylene-5-methoxy-2-oxazolidinone (a mixture of diastereomer 1:1)

$^1$H-NMR (δ, CDCl$_3$): 1.777 (d, J=7.3Hz, 3H), 1.781 (d, J=7.3Hz, 3H), 3.485 (s, 3H), 3.494 (s, 3H), 4.179 (d, J=2.4Hz, 1H), 4.191 (d, J=2.9Hz, 1H), 4.293 (d, J=2.9Hz, 1H), 4.296 (d, J=2.4Hz, 1H), 5.321 (q, J=7.3Hz, 1H), 5.363 (q, J=7.3Hz, 1H), 5.686 (s, 1H), 5.698 (s, 1H), 7.26–7.37 (m, 1OH)

IR (neat, cm$^{-1}$): 1772, 1668

MS (EI) m/z 233 (M$^+$)

EXAMPLE 20

Synthesis of 3-((S)-1-phenylethyl)-5-phenoxy-2(3H)-oxazolone

In a 25 ml-volume flask were charged 98 mg (0.99 mmol) of bistrichloromethylcarbonate and 3 ml of toluene, and after cooling the mixture to 0C, a mixed solution of 169 mg (0.66 mmol) of N-((S)-1-phenylethyl)-glycine phenyl ester, 100 mg (0.99 mmol) of triethylamine and 3 ml of toluene was added dropwise to the above mixture over 10 minutes. Thereafter, stirring was carried out for further 0.5 hour to effect the reaction.

After completion of the reaction, 5 ml of a saturated aqueous sodium chloride solution was added to the resulting reaction mixture (1). The liquids were separated and the organic layer was dried over anhydrous magnesium sulfate followed by filtration. To the filtrate was added 300 mg (3.0 mmol) of triethylamine and the mixture was reacted under stirring at 120° C. for 17 hours.

After completion of the reaction, insolubles were removed by filtration from the resulting reaction mixture (2). To the filtrate was added 5 ml of a saturated aqueous ammonium chloride solution, the liquids were separated and the organic layer was washed with 5 ml of a saturated aqueous sodium chloride solution. The washed organic layer was dried over anhydrous magnesium sulfate followed by filtration, and the filtrate was concentrated to obtain 182 mg (0.65 mmol) of 3-((S)-1-phenylethyl)-4-methyl-5-phenoxy-2(3H)-oxazolone as a brownish oily substance. (Yield based on N-((S)-1-phenylethyl)-glycine phenyl ester=98%)

IR (neat, cm$^{-1}$): 1687, 1772

$^1$H-NMR (δ, CDCl$_3$): 1.70 (d, J=6.8Hz, 3H), 5.37 (d, J=6.8 Hz, 1H), 5.88 (s, 1H), 7.03–7.40 (m, 1OH)

MS (EI) m/z 281 (M$^+$)

EXAMPLE 21

Synthesis of 3-benzyl-4-methyl-5-methoxy-2(3H)-oxazolone

In a 100 ml-volume flask were charged 1.04 g (10.5 mmol) of bistrichloromethylcarbonate and 30 ml of toluene, and after cooling the mixture to 0° C., a mixed solution of 1.35 g (7.00 mmol) of N-benzyl-alanine methyl ester, 1.06 mg (10.5 mmol) of triethylamine and 30 ml of toluene was added dropwise to the above mixture over 1.5 hours. Thereafter, stirring was carried out for further one hour to effect the reaction.

After completion of the reaction, 60 ml of a saturated aqueous sodium chloride solution was added to the resulting reaction mixture (1). The liquids were separated and the organic layer was dried over anhydrous magnesium sulfate followed by filtration. To the filtrate was added 1.06 g (10.5 mmol) of triethylamine and the mixture was heated at 100° C. for 3 hours, then raised to 120° C. and reacted under stirring for 3.5 hours.

After completion of the reaction, insolubles were removed by filtration from the resulting reaction mixture (2). To the filtrate was added 60 ml of a saturated aqueous ammonium chloride solution, the liquids were separated and the organic layer was washed with 60 ml of a saturated aqueous sodium chloride solution. The washed organic layer was dried over anhydrous magnesium sulfate followed by filtration, and the filtrate was concentrated to obtain 1.41 g (6.43 mmol) of 3-benzyl-4-methyl-5-methoxy-2(3H)-oxazolone as a brownish oily substance. (Yield based on N-benzyl-alanine methyl ester=92%)

IR (neat, cm$^{-1}$): 1722, 1776

$^1$H-NMR (δ, CDCl$_3$): 1.80 (s, 3H), 3.80 (s, 3H), 4.71 (s, 2H), 7.25–7.36 (m, 5H)

MS (EI) m/z 219 (M$^+$)

EXAMPLE 22

Synthesis of 3-(1-naphthyl)methyl-5-methoxy-2(3H)-oxazolone

In 150 ml of toluene was dissolved 28.0 g (122 mmol) of N-(1-naphthyl) methyl-glycine methyl ester to obtain a toluene solution. To the resulting toluene solution was added an aqueous solution in which 12.9 g of anhydrous sodium carbonate had been dissolved in 200 ml of water. The mixture was cooled to 0° C. under stirring and 18.1 g (183 mmol) of a phosgene gas was blown to react these materials. After completion of the blowing, the mixture was reacted for 2 hours, and further stirred at room temperature for one hour.

After completion of the reaction, the aqueous layer was separated from the resulting reaction mixture (1). The toluene layer was dried over anhydrous magnesium sulfate and filtered, and 24.7 g (244 mmol) of triethylamine was added to the filtrate and the mixture was heated to 120° C. for 12 hours. Then, 9.65 g (122 mmol) of pyridine was added to the mixture to effect reaction at 120° C. for 10 hours. After completion of the reaction, the resulting reaction mixture (2) was cooled to room temperature and precipitated amine hydrochloride was separated by filtration. The filtrate was washed with 100 ml of a saturated aqueous ammonium chloride solution and 100 ml of a saturated aqueous sodium chloride solution. The toluene layer was dried over anhydrous magnesium sulfate, followed by filtration, and the filtrate was concentrated under reduced pressure. The resulting residue was purified by applying to silica gel column chromatography (eluent; n-hexane:ethyl acetate=4:1 (volume ratio)) and recrystallization was carried out from a n-hexane and ethyl acetate mixed solution to obtain 13.3 g (52.2 mmol) of 3-(1-naphthyl)methyl-5-methoxy-2(3H)-oxazolone as white crystals. (Yield based on N-(1-naphthyl)-methyl-glycine methyl ester=43%)

Melting point: 80 to 82° C.

IR (KBr, cm$^{-1}$) : 1678, 1757

$^1$H-NMR ($\delta$, CDCl$_3$): 3.64 (s, 3H), 5.09 (s, 2H), 5.31 (s, 1H), 7.25–7.47 (m, 2H), 7.50–7.60 (m, 2H), 7.87 (m, 2H), 8.07 (m, 1H).

MS (EI) m/z 255 (M$^+$)

EXAMPLE 23

Synthesis of 3-(R)-1-phenylethyl-5-((I)-menthyloxy)-2(3H)-oxazolone

In 100 ml of acetonitrile was dissolved 5.82 g (48 mmol) of (R)-(+)-$\alpha$-methylbenzylamine, and to the solution was added an aqueous solution containing 6.08 g (44 mmol) of anhydrous potassium carbonate dissolved in water. The mixture was stirred under room temperature, and 1.09 g (40 mmol) of menthyl bromoacetate was added dropwise over 0.3 hour and after dropwise addition, the mixture was further stirred at room temperature for 3 hours. After completion of the reaction, the aqueous layer was separated from the resulting reaction mixture (1) and the organic layer was concentrated under reduced pressure. The aqueous layer was extracted with 50 ml of ethyl acetate, the extract was combined with the concentrate and the mixture was washed with 50 ml of water. The mixture was washed with 100 ml of an aqueous 3.6% hydrochloric acid solution, and then with 50 ml of water. The mixture was further washed with 100 ml of a saturated aqueous sodium hydrogen carbonate solution, and then with 50 ml of water. After drying over anhydrous magnesium sulfate, the mixture was concentrated under reduced pressure to obtain 12 g (37.8 mmol) of N-((R)-1-phenylethyl)glycine-(l)-menthyl ester as a colorless liquid. (Yield based on menthyl bromoacetate 94.5%)

MS: (CI, i-C$_4$H$_{10}$) m/z 318 (MH$^+$)

EA: Calcd: C, 75.67; H, 9.84; N, 4.41 Found: C, 75.53; H, 9.80; N, 4.26

IR: (KBr, cm$^{-1}$); 3339 (w) , 1734 (s)

$^1$H-NMR: ($\delta$, CDCl$_3$) 0.73 to 1.09 (m, 12H) , 1.36 (d, J=6.4Hz, 1H), 1.48 to 1.80 (m, 8H), 2.00 (S, 1H), 3.18 (d, J=17.6Hz, 1H), 3.29 (d, J=17.6Hz, 1H), 3.79 (q, J=6.4Hz, 1H), 4.73 (ddd, J=4.4Hz, 1H), 7.22 to 7.32 (m, 5H).

In 30 ml of toluene was dissolved 6.35 g (20 mmol) of the resulting N-((R)-1-phenylethyl)glycine-(l)-menthyl ester, and to the solution was added an aqueous solution of 1.17 g (11 mmol) of anhydrous sodium carbonate dissolved in water. The mixture was cooled to 15° C. and 2.18 g (22 mmol) of a phosgene gas was blown under stirring to react these materials. After completion of the phosgene blowing, the mixture was further stirred at room temperature for 1.5 hours After completion of the reaction, the aqueous layer was separated from the resulting reaction mixture (2). The toluene layer was dried over anhydrous magnesium sulfate followed by filtration, and 4.05 g (40 mmol) of triethylamine was added to the filtrate and the mixture was reacted at 120° C. for 2 hours. After completion of the reaction, the resulting reaction mixture (3) was cooled to room temperature, and the precipitated triethylamine hydrochloride was removed by filtration. The filtrate was washed with 100 ml of water, dried over anhydrous magnesium sulfate, and concentrated under reduced pressure. To the resulting concentrated residue was added 20 ml of methanol, and the mixture was cooled to 0 to 5° C. The precipitated crystals were collected by filtration and the resulting crystals were dried at 30° C. under reduced pressure to obtain 4.71 g (13.7 mmol) of 3-(R)-1-phenylethyl-5-((l)-menthyloxy)-2(3H)oxazolone as white crystals. (Yield based on N-((R)-1-phenylethyl) glycine-(l)-menthyl ester 68.6)

m.p.: 132.5 to 135° C.

$(\alpha)^{24}_D$=−15.4 (c 1.01, CHCl$_3$)

MS (CI, I-C$_4$H$_{10}$) m/z 344 (MH$^+$)

EA: Calcd: C, 73.44; H, 8.51; N, 4.08 Found: C, 73.17; H, 8.68; N, 4.05

IR (KBr, cm$^{-1}$): 1746 (s), 1671 (s)

$^1$H-NMR: ($\delta$, CDCl$_3$) 0.73 to 1.06 (m, 12H), 1.36 to 1.42 (m, 4H), 1.66 (d, J=6.8Hz, 3H), 2.04 to2.18 (m, 2H), 3.85 (ddd, J=4.4Hz, 1H), 5.33 (q, J=6.8Hz, 2H), 5.54 (s, 1H), 7.26 to 7.39 (m, 5H).

EXAMPLE 24

Synthesis of 3-(S)-1-phenylethyl-5-((l)-menthyloxy)-2(3H)oxazolone

In 100 ml of acetonitrile was dissolved 5.82 g (48 mmol) of (S)-(−)-$\alpha$-methylbenzylamine, and to the solution was added an aqueous solution containing 6.08 g (44 mmol) of anhydrous potassium carbonate dissolved in water. The mixture was stirred under room temperature, and 1.09 g (40 mmol) of menthyl bromoacetate was added dropwise over 0.3 hour and after dropwise addition, the mixture was further stirred at room temperature for 3 hours. After completion of the reaction, the aqueous layer was separated from the resulting reaction mixture (1) and the organic layer was concentrated under reduced pressure. The aqueous layer was extracted with 50 ml of ethyl acetate, the extract was combined with the concentrate and the mixture was washed with 50 ml of water. The mixture was washed with 100 ml of an aqueous 3.6% hydrochloric acid solution, and then with 50 ml of water. The mixture was further washed with 100 ml of a saturated aqueous sodium hydrogen carbonate solution, and then with 50 ml of water. After drying over anhydrous magnesium sulfate, the mixture was concentrated under reduced pressure to obtain 11.6 g (36.5 mmol) of N-((S)-1-phenylethyl)glycine-(l)-menthyl ester as a pale yellowish liquid. (Yield based on menthyl bromoacetate 91.3%)

MS: (CI, i-C$_4$H$_{10}$) m/z 318 (MH$^+$)

EA: Calcd: C, 75.67; H, 9.84; N, 4.41 Found: C, 75.42; H, 10.02; N, 4.48

IR: (KBr, cm$^{-1}$); 3339 (w), 1734 (s)

$^1$H-NMR: (δ, CDCl$_3$) 0.73 to 1.09 (m, 12H) , 1.36 (d, J=6.4Hz, 1H), 1.48 to 1.80 (m, 8H), 2.00 (s, 1H), 3.18 (d, J=17.6Hz, 1H), 3.29 (d, J=17.6Hz, 1H), 3.79 (q, J=6.4Hz, 1H), 4.73 (ddd, J=4.4Hz, 1H), 7.22 to 7.32 (m, 5H).

In 30 ml of toluene was dissolved 6.35 g (20 mmol) of the resulting N-((S)-1-phenylethyl) glycine-(l)-menthyl ester, and to the solution was added an aqueous solution of 1.17 g (11 mmol) of anhydrous sodium carbonate dissolved in water. The mixture was cooled to 15° C. and 2.18 g (22 mmol) of a phosgene gas was blown under stirring to react these materials. After completion of the phosgene blowing, the mixture was further stirred at room temperature for 1.5 hours. After completion of the reaction, the aqueous layer was separated from the resulting reaction mixture (2). The toluene layer was dried over anhydrous magnesium sulfate followed by filtration, and 4.05 g (40 mmol) of triethylamine was added to the filtrate and the mixture was reacted at 120° C. for 2 hours. After completion of the reaction, the resulting reaction mixture (3) was cooled to room temperature, and the precipitated triethylamine hydrochloride was removed by filtration. The filtrate was washed with 100 ml of water, dried over anhydrous magnesium sulfate, and concentrated under reduced pressure. To the resulting concentrated residue was added 150 ml of hexane, and the mixture was cooled to 0 to 5° C. The precipitated crystals were collected by filtration and the resulting crystals were dried at 30° C. under reduced pressure to obtain 4.65 g (13.5 mmol) of 3-(S)-1-phenylethyl-5-((l)-menthyloxy)-2(3H)oxazolone as white crystals. (Yield based on N-((S)-1-phenylethyl) glycine-(l)-menthyl ester 67.7%)

m.p.: 118 to 120° C.

$(\alpha)^{24}_D$=−122.7 (c 1.02, CHCl$_3$)

MS (CI, I-C$_4$H$_{10}$) m/z 344 (MH$^+$)

EA: Calcd: C, 73.44; H, 8.51; N, 4.08 Found: C, 73.41; H, 8.74; N, 4.08

IR (KBr, cm$^{-1}$): 1746 (s), 1671 (s)

$^1$H-NMR: (δ, CDCl$_3$) 0.73 to 1.06 (m, 12H), 1.36 to 1.42 (m, 4H), 1.66 (d, J=6.8Hz, 3H), 2.04 to2.18 (m, 2H), 3.85 (ddd, J=4.4Hz, 1H) , 5.33 (q, J=6.8Hz, 2H), 5.54 (s, 1H), 7.26 to 7.39 (m, 5H).

EXAMPLE 25

Synthesis of 3-phenyl-4-methyl-5-methoxy-2(3H)-oxazolone

In 35 ml of toluene was dissolved 4.48 g (25 mmol) of methyl 2-(N-phenyl) amino-propionate, and to the solution was added an aqueous solution containing 1.46 g (13.8 mmol) of anhydrous sodium carbonate dissolved in water. The mixture was cooled to 15° C. and 2.72 g (27.5 mmol) of a phosgene gas was blown under stirring to carry out the reaction. After completion of the phosgene blowing, the mixture was further stirred at room temperature for 7 hours. After completion of the reaction, the aqueous layer was separated from the resulting reaction mixture (1). The toluene layer was dried over anhydrous magnesium sulfate followed by filtration, and 2.53 g (25 mmol) of triethylamine was added to the filtrate and the mixture was reacted at 120° C. for 12 hours. After completion of the reaction, the resulting reaction mixture (2) was cooled to room temperature, and the precipitated triethylamine hydrochloride was removed by filtration. The filtrate was washed with 100 ml of water, dried over anhydrous magnesium sulfate, and concentrated under reduced pressure. The resulting concentrated residue was applied to silica gel column chromatography (eluent; hexane:ethyl acetate=10:1 (volume ratio)) to obtain 3.51 g (17.1 mmol) of 3-phenyl-4-methyl-5-methoxy-2(3H)oxazolone as pale yellowish crystals. (Yield based on 2- (N-phenyl) amino propionate 68%)

m.p.: 81 to 83.5° C.

MS (EI) m/z 205 (M$^+$), 118, 77

$^1$H-NMR: (δ, CDCl$_3$) 1.84 (s, 3H), 3.89 (s, 3H), 7.25 to 7.51 (m, 5H).

EXAMPLE 26

Synthesis of 3-(3,4-dimethoxybenzyl)-5-methoxy-2 (3H)oxazolone

In 30 ml of toluene was dissolved 4.78 g (20 mmol) of N-(3,4-dimethoxybenzyl)-glycine-methyl ester, and to the solution was added an aqueous solution containing 1.17 g (11 mmol) of anhydrous sodium carbonate dissolved in water. The mixture was cooled to 15° C. and 2.18 g (22 mmol) of a phosgene gas was blown under stirring to carry out the reaction. After completion of the phosgene blowing, the mixture was further stirred at room temperature for 2 hours. After completion of the reaction, the aqueous layer was separated from the resulting reaction mixture (1). The toluene layer was dried over anhydrous magnesium sulfate followed by filtration, and 2.02 g (20 mmol) of triethylamine was added to the filtrate and the mixture was reacted at 120° C. for 17 hours. After completion of the reaction, the resulting reaction mixture (2) was cooled to room temperature, and the precipitated triethylamine hydrochloride was removed by filtration. The filtrate was washed with 100 ml of water, dried over anhydrous magnesium sulfate, and concentrated under reduced pressure. The resulting concentrated residue was applied to silica gel column chromatography (eluent; hexane:ethyl acetate=4:1 (volume ratio)) to obtain 1.74 g (4.8 mmol) of 3-(3,4-dimethoxybenzyl)-5-methoxy-2(3H)oxazolone as white crystals. (Yield based on N-(3,4-dimethoxybenzyl)-glycine-methyl ester 32.8%)

m.p.: 99.5 to 102° C.

MS (EI) m/z 265 (M$^+$), 151

$^1$H-NMR: (δ, CDCl$_3$) 3.73 (s, 3H), 3.87 (s, 3H), 3.88 (s, 3H), 4.60 (s, 2H), 5.40 (s, 1H), 6.80 to 6.85 (m, 3H).

REFERENCE EXAMPLE 1

Synthesis of 3-diphenylmethyl-4-carbomethoxy-5-phenyloxazolidinone

In 4 ml of methylene chloride were dissolved 0.281 g (1.0 mmol) of 3-diphenylmethyl-5-methoxy-2(3H)-oxazolone and 0.106 g (I.0 mmol) of benzaldehyde, and under argon atmosphere, the mixture was cooled to −78° C. To the mixture was added 14 mg (0.1 mmol) of BF$_3$.ET$_2$O, and the mixture was reacted as it were at −78° C. for 2 hours.

After completion of the reaction, the temperature of the resulting reaction mixture (1) was raised to about −20° C., 15 ml of a saturated aqueous sodium hydrogen carbonate solution was added, and the mixture was extracted with 10 ml of methylene chloride. The organic layer was washed with a saturated sodium chloride solution, dried over magnesium sulfate and concentrated under reduced pressure to obtain 3-diphenylmethyl-4-carbomethoxy-5-phenyloxazolidinone quantitatively as white crystals (0.4 g). The formation ratio of a diastereomer ratio (syn/anti) of the formed products was 2/96 by HPLC analysis.

Melting point: 99 to 102° C.

IR (KBr, cm$^{-1}$): 1760

$^1$H-NMR (δ, CDCl$_3$) (anti isomer): 3.40 (s, 3H), 4.21 (d, J=3.9Hz), 5.44 (d, J=3.9Hz, 1H), 6.27 (s, 1H), 7.0 to 7.45 (m, 15H)

MS (CI, i-C$_4$H$_{10}$) m/z 388 (MH$^+$)

What is claimed is:

1. A 5-alkoxy-2(3H)-oxazolone compound represented by the formula (I):

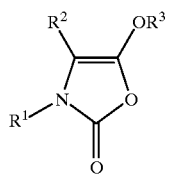

wherein $R^1$ represents a hydrogen atom, a $C_1$ to $C_{10}$ alkyl group which may be substituted, a $C_3$ to $C_{10}$ cycloalkyl group which may be substituted, a $C_2$ to $C_{10}$ alkenyl group which may be substituted or a phenyl group which may be substituted; $R^2$ represents a hydrogen atom, a $C_1$ to $C_{10}$ alkyl group which may be substituted, a phenyl group which may be substituted or an unsubstituted $C_2$ to $C_{10}$ alkenyl group; and $R^3$ represents a $C_1$ to $C_{10}$ alkyl group which may be substituted, a $C_3$ to $C_{10}$ cycloalkyl group which may be substituted, a $C_2$ to $C_{10}$ alkenyl group which may be substituted, provided that a 2-alkenyl group is excluded, or a phenyl group which may be substituted.

2. The 5-alkoxy-2 (3H)-oxazolone compound according to claim 1, wherein $R^1$ represents a $C_1$ to $C_6$ alkyl group which may be substituted, a $C_3$ to $C_6$ cycloalkyl group which may be substituted, a $C_2$ to $C_4$ alkenyl group which may be substituted or a phenyl group which may be substituted; $R^2$ represents a hydrogen atom, a $C_1$ to $C_6$ alkyl group which may be substituted or an unsubstituted $C_2$ to $C_4$ alkenyl group; and $R^3$ represents a $C_1$ to $C_6$ alkyl group which may be substituted, a $C_3$ to $C_6$ cycloalkyl group which may be substituted, a $C_3$ to $C_{10}$ alkenyl group which may be substituted, provided that a 2-alkenyl group is excluded, or a phenyl group which may be substituted.

3. The 5-alkoxy-2 (3H)-oxazolone compound according to claim 1, wherein $R^1$ represents a $C_1$ to $C_4$ alkyl group which may be substituted, a cyclohexyl group, a $C_2$ to $C_3$ alkenyl group which may be substituted or a phenyl group which may be substituted; $R^2$ represents a hydrogen atom, a $C_1$ to $C_4$ alkyl group which may be substituted or an unsubstituted $C_2$ to $C_3$ alkenyl group; and $R^3$ represents a $C_1$ to $C_4$ alkyl group which may be substituted, a cyclohexyl group which may be substituted, a $C_4$ to $C_5$ alkenyl group which maybe substituted, provided that a 2-alkenyl group is excluded, or a phenyl group which may be substituted.

4. The 5-alkoxy-2 (3H)-oxazolone compound according to claim 1, wherein $R^1$ represents an unsubstituted $C_1$ to $C_6$ alkyl group which may be substituted, a $C_1$ to $C_4$ alkyl group which is substituted by an aryl group which may be substituted or by a heteroaromatic ring group which may be substituted, or a phenyl group; $R^2$ represents a hydrogen atom or a $C_1$ to $C_4$ alkyl group which may be substituted; and $R^3$ represents a $C_1$ to $C_4$ alkyl group which may be substituted, a cyclohexyl group which may be substituted, a $C_4$ to $C_5$ alkenyl group which may be substituted, provided that a 2-alkenyl group is excluded, or a phenyl group.

5. The 5-alkoxy-2 (3H)-oxazolone compound according to claim 1, wherein $R^1$ represents a benzyl group, a 4-methylbenzyl group, a 3,4-dimethoxybenzyl group, an 1-phenylethyl group, a diphenylmethyl group, a (1-naphthyl)methyl group, a (1-naphthyl) ethyl group, a furfuryl group, an isopropyl group or a phenyl group; $R^2$ represents a hydrogen atom, a methyl group, an ethyl group, a propyl group or an isopropyl group; and $R^3$ represents a methyl group, an ethyl group, a propyl group, an isopropyl group, a 4-pentenyl group, a cyclohexyl group, a menthyl group, a 8-phenylmenthyl group or a phenyl group.

6. The 5-alkoxy-2 (3H)-oxazolone compound according to claim 1, wherein the compound represented by the formula (I) is selected from the group consisting of 3-isopropyl-5-methoxy-2(3H)-oxazolone, 3-benzyl-5-methoxy-2(3H)-oxazolone, 3-(4-methylbenzyl)-4-methyl-5-methoxy-2(3H)-oxazolone, 3-(3,4-dimethoxybenzyl)-5-methoxy-2(3H)-oxazolone, 3-(1-phenylethyl)-5-methoxy-2 (3H)-oxazolone, 3-((S)-1-phenylethyl)-5-isopropoxy-2 (3H)-oxazolone, 3-((R)-1-phenylethyl)-5-methoxy-2(3H)-oxazolone, 3-((R)-1-(1-naphthyl)ethyl-5-methoxy-2(3H)-oxazolone, 3-((R)-1-(1-naphthyl)ethyl)-5-isopropoxy-2 (3H)-oxazolone, 3-diphenylmethyl-4-methyl-5-methoxy-2-(3H)-oxazolone, 3-diphenylmethyl-5-methoxy-2(3H)-oxazolone, 3-diphenylmethyl-5-((l)-menthyloxy)-2(3H)-oxazolone, 3-diphenylmethyl-5-((1S,2S, 5R)-5-methyl-2-(1-methyl-1-phenylethyl)cyclohexyloxy)-2(3H)-oxazolone, 3-furfuryl-4-ethyl-5-methoxy-2(3H)-oxazolone, 3-furfuryl-4-ethyl-5-(4-pentenyl)oxy-2(3H)-oxazolone, 3-isopropyl-4-methyl-5-cyclohexyloxy-2(3H)-oxazolone, 3-isopropyl-4-methyl-5-methoxy-2(3H)-oxazolone, 3-isopropyl-4-methyl-5-ethoxy-2(3H)-oxazolone, 3-benzyl-5-(l)-menthyloxy)-2 (3H)-oxazolone, 3-((R)-1-phenylethyl)-4-methyl-5-methoxy-2(3H)-oxazolone, 3-((S)-1-phenylethyl)-5-phenoxy-2(3H)-oxazolone, 3-benzyl-4-methyl-5-methoxy-2 (3H)-oxazolone, 3-(1-naphthyl)methyl-5-methoxy-2(3H)-oxazolone, 3-((R)-1-phenylethyl)-5-((l)-menthyloxy)-2 (3H)-oxazolone, 3-((S)-1-phenylethyl)-5-((l)-menthyloxy)-2(3H)-oxazolone and 3-phenyl-4-methyl-5-methoxy-2(3H)-oxazolone.

7. A process for preparing the 5-alkoxy-2(3H)-oxazolone compound represented by the formula (I) according to claim 1, which comprises reacting a N-substituted-a-amino acid ester represented by the formula (II):

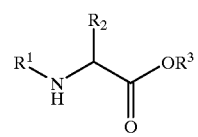

wherein $R^1$, $R^2$ and $R^3$ have the same meanings as defined above,
and a chloroformylating agent in the presence of a base (1), in a solvent to make it to a compound represented by the formula (III):

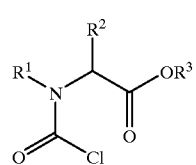

wherein $R^1$, $R^2$ and $R^3$ have the same meanings as defined above,
and then, subjecting to intramolecular cyclization reaction in the presence of a base (2).

8. The process according to claim 6, wherein the chloroformylating agent is phosgene, trichloromethylchloroformate or bistrichloromethylcarbonate.

* * * * *